US006027876A

United States Patent [19]
Kreitman et al.

[11] Patent Number: 6,027,876
[45] Date of Patent: Feb. 22, 2000

[54] METHOD FOR MONITORING PESTICIDE RESISTANCE

[76] Inventors: Martin Kreitman, 5760 S. Blackstone Ave., Chicago, Ill. 60637; Martin Taylor, 2246 E. 6th St., Tuscon, Ariz. 87519; Bruce C. Black, 286 Forest Rd., Yardley, Pa.

[21] Appl. No.: 07/998,289

[22] Filed: Dec. 30, 1992

[51] Int. Cl.[7] .............................. C12Q 1/68; C21N 1/00; C21N 5/10; C21N 15/12; C21N 15/63

[52] U.S. Cl. ........................... 435/6; 536/23.5; 536/24.5; 435/252.3; 435/325; 435/254.11; 435/320.1; 435/252.33

[58] Field of Search .......................... 435/252.3, 252.33, 435/320.1, 240.1, 254.11, 325, 6; 536/23.5, 24.5

[56] References Cited

FOREIGN PATENT DOCUMENTS 0 492 113 A2  7/1992  European Pat. Off. .

OTHER PUBLICATIONS

Salkoff et al. (1987) Science 237: 744–749.
Campanhola and Plapp (1989), *J. Econ. Entomol.*, 82:1577–1533.
Loughney et al. (1989), *Cell* 58:1143–1154.
Oakeshott et al. (1987), *PNAS USA* 84:3359–3363.
Karunaratre et al. (1991), *Resist, Pest. Manag. Newsletter* 3:11–13.
Fournier et al. (1989), *J. Mol. Biol.* 210:15–22.
Brattstein et al. (1977), *Science* 196:1349–1352.
Brattstein et al. (1973), *Pesticide Biochem. Physiol.* 3:393.
Krieger et al. (1971), *Science* 172:579.
Matsumara, Toxicology Insecticides, Plenum Press, New York, 1975 Table of contents only.
Kadous et al. (1983), *Pestic. Biochem. Physiol.* 19:157–166.
Tanaka et al. (1984), *Pestic. Biochem. Physiol.* 22:117–127.
Ffrench–Constant et al. (1990), *J. Econ. Entomol.* 83:1733–1737.
Ffrench–Constant et al. (1991), *PNAS USA* 88:7209–7213.
Wilson et al. (1986), *Devel. Biol.* 118:190–201.
Georghiou et al. (1978), *J. Econ. Entolmol.* 71:544–547.
Dyte (1972), *Nature* 238:48–49.
Wing (1988), *Science* 241:467–469.
Spindler–Barth et al. (1991), *Arch. Ins. Biochem. and Phys.* 16:11–18.
Cherbas et al. (1988), *PNAS USA*, 85:2096–2100.
Yao et al. (1992), *Cell* 71:63–72.
Koelle et al. (1991), *Cell* 67:59–77.
Yadav et al. (1986), *PNAS USA* 83:4418–4422.
Stalker et al. (1985), *J. Biol. Chem.* 260:4724–4728.
Thompson et al. (1987), *EMBO J.* 6:2519–1523.
DasSarma et al. (1986), *Science* 232:1242–1244.
Arp et al. (1981),*Fungizider Mirt. Biol. Bundesant*, pp. 236–237.
Davidse (1981), *Neth. J. Plant Pathol.* 87:11–24.
Davidse (1985), *EPPO Bull.* 15:403–409.
Davidse (1981), *Neth. J. Plant Pathol.* 87:65–68.
Davidse (1981), *Experiment. Mycology* 7:344–361.
Schewe et al., in Modern Selective Fungicides, H. Lyr, ed. V.E.B. Gistan Fisher Vertag. Jene, 1987, pp. 149–161.
Keon et al. (1991), *Current Genetics* 19:475–481.
Ott et al. (1990), *Mol. Gen. Genet.* 223:169–179.
Kamakura et al. (1987), *Agric. Biol. Chem.* 51:3165–3168.
Clemons et al. (1971), *Pesticide Biochem. Physiol.* 1:32–43.
Hammerschlag et al. (1973), *Pesticide Biochem. Physiol.* 3:42–54.
Van Tuyl (1975), *Med. Fac. Lonbouww Ryksuniv. Gent.* 40:691–698.
Fanetra et al. (1991), *Mycol. Res.* 95:943–951.
Jung et al. (1990), *Cell Motility and the Cytoskeleton* 17:87–94.
Orbach et al. (1986), *Moll. Cell Biol.* 6:2452–2461.
Mullin et al (1992) ACS Symposium Series 505:1–13.
Doyde et al 1991 Insect Biochem 21:689–696.
Rogart et al 1989 Proc. Nat'l Acad Sci. USA 86 8170–8174.
Wahl et al 1987 Methods in Entomology 152 415–423.

*Primary Examiner*—Bradley Sisson
*Assistant Examiner*—G E Bugaisky
*Attorney, Agent, or Firm*—Darby & Darby

[57] ABSTRACT

The present invention relates to an isolated nucleic acid fragment comprising a nucleic acid sequence encoding a lepidopteran sodium channel, or portion thereof.

15 Claims, 21 Drawing Sheets

FIG. 1A

```
D.mel.
para
       1   ATGACAGAAGATTCCGACTCGATATCTGAGGAAGAACGCAGTTGTCCGTCCCTTTACCCGCGAATCATTGGTG
           ---------+---------+---------+---------+---------+---------+---------+---  75
           M  T  E  D  S  D  S  I  S  E  E  E  R  S  L  F  R  P  F  T  R  E  S  L  V Dm    76   CAAATCGAACAACGCCATTGCCGCTGAACATGAAAAGCAGAAGGAGCTGGAAAGAAAGAGAGCCGAGGAGGTG
           ---------+---------+---------+---------+---------+---------+---------+--- 150
           Q  I  E  Q  R  I  A  A  E  H  E  K  Q  K  E  L  E  R  K  R  A  E  G  E  V Dm   151   CCGCGATATGGTCGCAAGAAAAAGCAAGAAATCCGATATGACGAGGACGAGGATGAAGGTCCACAACCG
           ---------+---------+---------+---------+---------+---------+---------+--- 225
           P  R  Y  G  R  K  K  K  Q  K  E  I  R  Y  D  D  E  D  E  D  E  G  P  Q  P
           /\intron A                                /\B Dm   226   GATCCTACACTTGAACAGGGTGTGCCAATACCTGTTGTCCGATTGCAGGGCAGCTTCCCGCCGAATTGGCCTCCACT
           ---------+---------+---------+---------+---------+---------+---------+--- 300
           D  P  T  L  E  Q  G  V  P  I  P  V  R  L  Q  G  S  F  P  P  E  L  A  S  T Dm   301   CCTCTCGAGGATATCGATCCCTACTACAGCAATGTACTGACATTCGTAGTTGTAAGCAAAGGAAAAGATATTTTT
           ---------+---------+---------+---------+---------+---------+---------+--- 375
           P  L  E  D  I  D  P  Y  Y  S  N  V  L  T  F  V  V  V  S  K  G  K  D  I  F
                                                     /\C Dm   376   CGCTTTTCTGCATCAAAAGCAATGTGGATGCTCGATCCATTCAATCCGATACGTCGTGTGGCCATTTACATTCTA
           ---------+---------+---------+---------+---------+---------+---------+--- 450
           R  F  S  A  S  K  A  M  W  M  L  D  P  F  N  P  I  R  R  V  A  I  Y  I  L Dm   451   GTGCATCCATTATTTTCCCTATTCATCATCACCACAATTCTCGTCAACTGATCCTGATGATAATGCCGACAACG
           ---------+---------+---------+---------+---------+---------+---------+--- 525
           V  H  P  L  F  S  L  F  I  T  T  I  L  V  N  C  I  L  M  I  M  P  T  T
           I-S1
```

FIG. 1B

```
Dm   526 CCCACGGTTGAGTCCACTGAGGTGATATTCACCGGAATCTACACATTTGAATCAGCTGTTAAAGTGATGGCACGA 600
          P  T  V  E  S  T  E  V  I  F  T  G  I  Y  T  F  E  S  A  V  K  V  M  A  R
                            I-S2

Dm   601 GGTTTCATTTTATGCCCGTTTACGTACTTTAGAGATGCATGAATTGGCTGGACTTCGTAGTAATAGCTTTAGCT 675
          G  F  I  L  C  P  F  T  Y  L  R  D  A  W  N  W  L  D  F  V  V  I  A  L  A  /\D
                                              I-S3

Dm   676 TATGTGACCATGGGTATAGATTTAGGTAATCTAGCAGCCCTGCGAACGTTTAGGGTGCTGAGCGCTTAAAACC 750
          Y  V  T  M  G  I  D  L  G  N  L  A  A  L  R  T  F  R  V  L  R  A  L  K  T
                                            I-S4

SCp 788+                                             AArACnAThGTnCGnGC-->
Dm   751 GTAGCCATTGTGCCAGGCTTGAAGACCATCGTCGGCGCCGTCATCGAATCTGTGAAGAATCTGCGGATGTGATT 825
          V  A  I  V  P  G  L  K  T  I  V  G  A  V  I  E  S  V  K  N  L  R  D  V  I
              /\E                                                              I-S5

Dm   826 ATCCTGACCATGTTCTCCCTGTCGGTTCGCGTTGATGGCCTTACAGATCTATATGGCGTGCTCACCGAGAAG 900
          I  L  T  M  F  S  L  S  V  F  A  L  M  G  L  Q  I  Y  M  G  V  L  T  E  K

Dm   901 TGCATCAAGAAGTTCCCGCTTGACGGTTCCTGGGCAATCTGACCGACGAGAACTGGACTATCACAATCGCAAT 975
          C  I  K  K  F  P  L  D  G  S  W  G  N  L  T  D  E  N  W  D  Y  H  N  R  N
```

FIG. 1C

```
Dm  AGCTCCAATTGGTATTCCGAGGACGAGGGCATTCATTTCCGTTATGCGGCAATATCCGTGCGGGGCAATGC
976 ---------+---------+---------+---------+---------+---------+---------+ 1050
     S  S  N  W  Y  S  E  D  E  G  I  S  F  P  P  L  C  G  N  I  S  G  A  G  Q  C
                                                                        /\F

D&K+                        AAyCCnAAyTAyGGnTAyAC->
Doyle and Knipple's sequence                    S  F  D  S  F  G
Dm                                        AGTTTCGATTCATTCGGT
     GACGACGATTACGTGTGCCTGCAGGGGTTTGGTCCGAATTATGGCTACACCAGCTTCGATTCGTTCGGA
1051 ---------+---------+---------+---------+---------+---------+---------+ 1125
     D  D  D  Y  V  C  L  Q  G  F  G  P  N  P  N  Y  G  Y  T  S  F  D  S  F  G SCp 1153-                   <-TACTGnGTyCTrAArACC
D&K-                        <-TACTGnGTyCTrAArACCCTy
D&K      W  A  F  L  S  A  F  R  L
     TGGGCTTTCCTGTGCCGGCGTTTCGTCTC
     TGGGCTTTCCTGTCCGGCGCCTTCCGGCTGATGACACAGGACTTCTGGGAGGATCTGTACCAGCTGGTGTTGCGCGCC
Dm   ---------+---------+---------+---------+---------+---------+---------+ 1200
1126  W  A  F  L  S  A  F  R  L  M  T  Q  D  F  W  E  D  L  Y  Q  L  V  L  R  A Dm   GCCGGACCATGGCACATGCTGTTCTTTATAGTCATCATCTTCCTAGTTCATTCTATCTTGTGAATTGATTTTG
1201 ---------+---------+---------+---------+---------+---------+---------+ 1275
     A  G  P  W  H  M  L  F  F  I  V  I  I  F  L  G  S  F  Y  L  V  N  L  I  L
                       I-S6
```

FIG. 1D

```
Dm  1276  GCCATTGTTGCCATGTCGTATGACGAATTGCAAAGAAGGCCGAAGAAGAGGCTGCCGAAGAGGAGGCGATA  1350
           A  I  V  A  M  S  Y  D  E  L  Q  R  K  A  E  E  E  A  A  E  E  E  A  I

Dm  1351  CGTGAAGCGGAAGAAGCTGCCGCCGCCAAAGCGGCCAAGCTGGAGGAGCGGGCCAATGCGCAGGCTCAGGCAGCA  1425
           R  E  A  E  E  A  A  A  A  K  A  A  K  L  E  E  R  A  N  A  Q  A  Q  A  A

Dm  1426  GCGGATGCGGCTGCCGCCGAAGAGGCTGCACTGCATCCGGAAATGGCCAAGAGTCCGACGTATTCTTGCATCAGC  1500
           A  D  A  A  A  E  E  A  A  L  H  P  E  M  A  K  S  P  T  Y  S  C  I  S

Dm  1501  TATGAGCTATTTGTTGGCGGCGAGAAGGGCAACGATGACAACAACAAAGAGAAGATGTCCATTCGGAGCGTGAG  1575
           Y  E  L  F  V  G  G  E  K  G  N  D  D  N  N  K  E  K  M  S  I  R  S  V  E

Dm  1576  GTGGAGTCGGAGTCGGTGAGCGTTATACAAAGACAACCAGCACCTACCACAGCACCAAGCTACCAAAGTTCGT  1650
           V  E  S  E  S  V  S  V  I  Q  R  Q  P  A  P  T  T  A  H  Q  A  T  K  V  R
                                      /\G

Dm  1651  AAAGTGAGCACGTACACGATACGGAACGACGTGGCCGCTTTGGTATACCCGGTAGCGATCGTAAGCCATTGGTA  1725
           K  V  S  T  Y  T  I  R  N  G  R  F  G  I  P  G  S  D  R  K  P  L  V
                               /\alt. exon A 63bp Dm  1726  TTGTCAACATATCAGGATGCCCAGCAGCACTTGCCCTATGCCGACGACTCGAATGCCGTCACCCGATGTCCGAA  1800
           L  S  T  Y  Q  D  A  Q  Q  H  L  P  Y  A  D  D  S  N  A  V  T  P  M  S  E
```

FIG. 1E

```
       GAGAATGGGGCCATCATAGTGCCCGTGTACTATGGCAATCTAGGCTCCCGACACTCATGTGTATACCTGCATCAG
 1801  ---------+---------+---------+---------+---------+---------+---------+-----  1875
Dm      E  N  G  A  I  I  V  P  V  Y  Y  G  N  L  G  S  R  H  S  S  Y  T  S  H  Q

TCCCGAATATATCGTATACCTCACATGGCGATCTACTCGGCGGCCGTCATGGGCGTCAGCACAATGACCAAG
 1876  ---------+---------+---------+---------+---------+---------+---------+-----  1950
Dm      S  R  I  S  Y  T  S  H  G  D  L  L  G  G  M  A  V  M  G  V  S  T  M  T  K

GAGAGCAAATTGCGCAACCGCAACACACGCAATCAATCAGTGGGCGCCACCAATGGCGGCACCACCTGTCTGGAC
 1951  ---------+---------+---------+---------+---------+---------+---------+-----  2025
Dm      E  S  K  L  R  N  R  N  T  R  N  Q  S  V  G  A  T  N  G  G  T  T  C  L  D

ACCAATCACAAGCTCGATCATCGCGACTACGAAATTGGCCTCGAGTGCACGGACGAAGCTGGCAAGATTAAACAT
 2026  ---------+---------+---------+---------+---------+---------+---------+-----  2100
Dm      T  N  H  K  L  D  H  R  D  Y  E  I  G  L  E  C  T  D  E  A  G  K  I  K  H

CATGACAATCCTTTTATCGAGCCCGTCCAGACACAAACGGTGGTTGATATGAAAGATGTGATGGTCCTGAATGAC
 2101  ---------+---------+---------+---------+---------+---------+---------+-----  2175
Dm      H  D  N  P  F  I  E  P  V  Q  T  Q  T  V  V  D  M  K  D  V  M  V  L  N  D

ATCATCGAACAGGCCGCTGGTCGGCACAGTCGGGCAAGCGATCGCGGTGTCTCCGTTACTATTTCCCAACAGAG
 2176  ---------+---------+---------+---------+---------+---------+---------+-----  2250
Dm      I  I  E  Q  A  A  G  R  H  S  R  A  S  D  R  G  V  S  V  Y  F  P  T  E
                                                         /\H <-- alt exon B --> /\I GACGATGATGACGAGGATGGGCCGACGTTCAAAGACAAGGCACTCGAAGTGATCCTCAAAGGCATCGATGTGTTTGT
 2251  ---------+---------+---------+---------+---------+---------+---------+-----  2325
Dm      D  D  D  E  D  G  P  T  F  K  D  K  A  L  E  V  I  L  K  G  I  D  V  F  C
```

FIG. 1F

```
Dm  2326 GTGTGGGACTGTTGCTGGGTTTGGTTGAAATTTCAGGAGTGGGTATCGCTCATCGTCTTCGATCCCTTCGTCGAG 2400
          V  W  D  C  C  W  V  L  K  F  Q  E  W  V  S  L I V F D P F V E
                                                        II-S1

Dm  2401 CTCTTCATCACGCTGTGCATTGTGGTCAACACGATGTTCATGGCAATGGATCACCACGATATGAACAAGGAGATG 2475
          L  F  I  T  L  C  I  V  V  N  T  M  F  M  A  M  D  H  H  D  M  N  K  E  M
          II-S2

Dm  2476 GAACGCGTGCTCAAGAGTGGCAACTATTTCTTCACCGCCACCTTTGCCATCGAGGCCACCATGAAGCTAATGGCC 2550
          E  R  V L K S G N Y F F T A T F A I E A T M K L M  A

Dm  2551 ATGAGCCCCAAGTACTATTTCCAGGAGGGCTGGAACATCTTCGACTTCATTATCGTGGCCCTATCGCTATTGGAA 2625
          M  S  P  K  Y  Y  F  Q  E  G  W  N  I  F  D  F  I  I  V  A  L  S  L  L  E
                                     II-S3

Dm  2626 CTGGGACTGGAGGGTGTCCAGGGTCTGTCCGTATTGCGTTCCTTTCGATTGCTGCGTGTATTCAAACTGGCCAAG 2700
          L  G  L  E  G  V  Q  G  L  S  V L R S F R L L R V F K L A K
                                                       /\J

Dm  2701 TCTTGGCCCCACACTTAATTACTCATTTCGATTATGGACGACACCATGGGGCGCTTTGGGTAATCTGACATTTGTA 2775
          S  W  P  T  L  N L L I S I M G R T M G A L G N L T F V
```

FIG. 1G

```
                                                 II-S5
        CTTTGCATTATCATCTTCATCTTTGCGGTGATGGAATGCAACTGTTCGGAAAGAATTATCATGATCACAAGGAC
Dm 2776 ----+----+----+----+----+----+----+----+----+----+----+----+----+----+---- 2850
         L  C  I  I  F  I  F  A  V  M  G  M  Q  L  F  G  K  N  Y  H  D  H  K  D
                                                                              /\K

CGCTTTTCCGGATGGCGACCTGCCGCGCTGGAACTTCACCGACTTTATGCACAGCTTCATGATCGTGTTCCGGGTG
Dm 2851 ----+----+----+----+----+----+----+----+----+----+----+----+----+----+---- 2925
         R  F  P  P  D  G  D  L  P  R  W  N  F  T  D  F  M  H  S  F  M  I  V  F  R  V

CTCTGCGGAGAATGGATCGAGTCCATGTGGGACTGCATGTACGTGGGCGATGTCTCGTGCATTCCCTTCTTCTTG
Dm 2926 ----+----+----+----+----+----+----+----+----+----+----+----+----+----+---- 3000
         L  C  G  E  W  I  E  S  M  W  D  C  M  Y  V  G  D  V  S  C  I  P  F  F  L
                                                              II-S6

GCCACCGTTGTCATCGGCAATCTTGTGGTACTTAACCTTTTCTTAGCCTTGCTTTTGTCCAATTTTGGCTCATCT
Dm 3001 ----+----+----+----+----+----+----+----+----+----+----+----+----+----+---- 3075
         A  T  V  V  I  G  N  L  V  V  L  N  L  F  L  A  L  L  L  S  N  F  G  S  S

AGCTTATCAGCGCCGACTGCCGATAACGATACGAATAAAATAGCCGAGCCTTCAATGAATTGGCCGATTAAA
Dm 3076 ----+----+----+----+----+----+----+----+----+----+----+----+----+----+---- 3150
         S  L  S  A  P  T  A  D  N  D  T  N  K  I  A  E  A  F  N  R  R  I  G  R  F  K

AGTTGGGTTAAGCGTAATATTGCTGATTGTTTCAAGTTAATACGTAACAAATCAAATAAGTGATCAA
Dm 3151 ----+----+----+----+----+----+----+----+----+----+----+----+----+----+---- 3225
         S  W  V  K  R  N  I  A  D  C  F  K  L  I  R  N  K  L  T  N  Q  I  S  D  Q
```

...CATAA-> no intron
             H  K  I  R  S  F  K  D  E  S  H  K  G  S  A  D  T  I  D  G  ?  ?  ?  K  D
scd61   CATAAAAtCAGGTCGTTCGTTCAAAGATGaATAAgTCaTAaAGTTCCGACAGACAGATGgCGamgmGmGAAGGAC
Dm      CATAAGAATCGACCATTCAAGGACGAGAACGAGCCACAAGGCCAGCGCCGAGACGATGAGGAGAAGCGCGAC
        3451 ---------+---------+---------+---------+---------+---------+---------+ 3525
             H  K  N  R  P  F  K  D  E  S  H  K  G  S  A  E  T  M  E  G  E  E  K  R  D
                      /\intron M A  S  K  E  E  L  G  L  E  E  E ..
scd61   GCTaGTAAAGAGGAATTGGGTTTAGAAGAAGGTCAGTGTAAAACTGCAATThAAAATTAACAGAATTGAACTAAG
Dm      GCCAGCAAGAAGGAGGATTTAGTGTCTCGACGAGG
        ---------+---------+---------+------ no intron
             A  S  K  E  D  L  G  L  D  E  E ..

scd61   CCATATATTGGA

..M  V  E  E  E  E  D  G  K  L  D  G  G  L  G  K
scd61   CAATTTGCATATAATTAATGTGTTACAGAATGTTGAAGAAGAGAGGAAGATGGGAAATGCGAGGAGGTCTAGGCAAA
Dm      AACTGGACGAGGAGGGCGAATGCGAGGAGGGCCCTCGAGGAGGGCCCCTCGACGGT
        ---------+---------+---------+---------+---------+---------+---------+ 3600
                                                      ..L  D  E  E  G  E  C  E  E  G  P  L  D  G T  D  I  I  V  A  A  D  E  E  V  V  D  D  S  P  A  D  C  C  P  E  P  C  Y
scd61   ACAGaCATTATAGTGTGGCCGCAGaTGAAGAAGTTGTTGACGATAGCCCTGCTGACTGCTGTCCAGAGCCGTTAC
Dm      GATATCATTATTCATGCACACGAGGATATACTTCGATGAATATCCAGCTGATTGCTGCCCGATTGCTGACTAT
        3601 ---------+---------+---------+---------+---------+---------+---------+ 3675
             D  I  I  H  A  H  D  E  D  I  L  D  E  Y  P  A  D  C  C  P  D  S  Y  Y

```
                A   K   F   P   F   L   V   G   D   D   E   S   P   F   W   Q   G   W   G   M   L   R   L   K   T
scd61           GCGAAGtTTCCATTCCTTGTGGGTGATGATGAATCTCCCTTTTGGCAAGGCTGGGGCATGCTTCGgTTGAAAACc
Dm              AAGAAATTTCCGATCTTAGCCGGTGACGATGACTCGCCGTTCTGGCAAGGATGGGGCAATTTACGACTGAAAACT
        3676    ----+----+----+----+----+----+----+----+----+----+----+----+----+----+---  3750
                K   K   F   P   I   L   A   G   D   D   D   S   P   F   W   Q   G   W   G   N   L   R   L   K   T F   K   L   I   E   N   T   Y   F   E   T   A   V   I   T   M   I   L   L   S   S   L   A   L
scd61           TTCAAACTCATTGAGAACACATATTTCGAAACGGCTGTGATTACAACGGCTGTTGCTCAGTAGTTTGGCTTTGTA
Dm              TTTCGATTAATTGAGGATAAATATTTTGAAACAGCTGTTATCACTATGATTTTAATGAGTAGCTTAGCTTTG
        3751    ----+----+----+----+----+----+----+----+----+----+----+----+----+---       no intron
                F   R   L   I   E   D   K   Y   F   E   T   A   V   I   T   M   I   L   M   S   S   L   A   L
                        III-S1 scd61           AGTTCTCAAATAA

A
scd61           TTTTCTGAACACTTGTTTCACATAGTAAGGGAGCAAATTATGTTCATGACGAAACTTykCTGTCTTTACAGGCT
Dm                                                                                              GCA          3825
                                                                                     no intron --- A L   E   D   V   N   L   P   H   R   P   I   L   Q   D   I   L   Y   Y   Y   M   D   R   I   F   T   V
scd61           TTAGAAGATGTAAATTTACCACATCGACCGATTCTTCAAGATATCTTGTATTATATGGATCGGATCTTCACCGTC
Dm              TTAGAAGATGTACATCTGCCACAAGACCCATATCGCAGGATATTTTATACTATATGGACAGAATATTTACGGTT
        3826    ----+----+----+----+----+----+----+----+----+----+----+----+----+----+---  3900
                L   E   D   V   H   L   P   Q   R   P   I   L   Q   D   I   L   Y   Y   M   D   R   I   F   T   V
                                                                        III-S2
```

FIG. 1K

```
hscp3868-                                                    <-CCACGACC..
Scp 3975+ "4229+/3985+"                         ACnAAyGCnTGGTGyTGG->
            I F F I E  M L I K W L A L G F Q K Y E T N A W C W
scd61     ATTTTCTTCATCGAGATGTTGATCAAATGGCTTGCCCTTGCCTTCCAGAAATACTTCACAAATGCGTGGTGCTGG
Dm        ATATTCTTCTTGAAATGTTAATCAAGTGGTTGGCGCTTCGGCTTCAAAGTGTACTTGACCAACGCGTGGTGTTGG
     3901 ---------+---------+---------+---------+---------+---------+---------+---- 3975
            I F F L E M L I K W L A L G F K V Y L T N A W C W
                                                            III-S3 hscp3868-GAGCTGAAGTAGTA
         L D F I V M
scd61    CTCGACTTCATCATTGTCATGTTCGTATCATTGAACTAACAGTTTCCT
Dm       CTCGATTTCGTGATTGTCATG
    3976 ---------+-------- intron N
           L D F V I V M
```

```
scd61   TGCAGAGATTAGATTTGGTAAAACGTAGATTATGATTATgGAATTTGAACTTGTAAGTTCTGTATAATGTGAAAGACA
scd61   AAATTAAgAGTTCAGGTCGGTCTTTGAAGTTTATCCTgCCGCCTCTCAGCGAGCTAAAGCTGGAAGAATAATTTA
scd61   TACAGTGTTAAGTATACCTAGATGTAAGGAATATATTGTATACTAAAGTAAATgACGATTGGTGTGGCGTTAGTT
scd61   GTCGCTcGTAAACCACGnGCAGTGATgsTGGcgsGACgACATCCCnGTTCcGCTCGAtGcACgTTGngngCGCT
scd61   GCGGcTCCGcGCGGTCTCCGCTgGGAGGGCATgCGCGTGACTTCTTCTGCTGAGAGGAcggCaCCACTCGTGCGCAGGCTGTGT
scd61   TGGTATCGTTGCGCTGCACATCCAGCCAACCAAACTTGTGACAGAGATTTTTATCGAaCCACtTTGTGAAATGTGAACTCTGA
scd61   GCTAATCGAAATAAGCAACCAACCAAACTCTTAATAAGTTGTTGATGTTGTTCTAATTTCTACTGTGTTGACGTGCAGCGCA
scd61   TTCATATTCAACTCTAATCTCTTAATTGTTCGATGTTCAGTGCAGTTCATGTGACTCTATAACCGACCCCcGCTATATGA
scd61   ACTCAAAGCGTGCAGCTTCGATTGTTTGTTTATGGAAAACCTCACAGAGTGACTTGAAATCCTTATACtTTCAAGTGCaTGaAACAAC
scd61   AgCTCTCGATGTCGTATTGTTTGTTTATGGAAAACCTCACAGAGTGACTTGAAATCCTTATACtTTCAAGTGCaTGaAACAAC
scd61   ATACCTGTGrCCGTATATATATaAAAACCTCACAGAGTGACTTGAAATCCTTATACtTTCAAGTGCaTGaAACAAC
```

FIG. 1L

```
scd61    ACGTCTTCTATCTTTGTGCTGTTGtGcGAGATAGTGCGTTTTCACGTACTACTCACATTACCCACATCTGTCGGG
scd61    GATAAATCCGAsATTTGAAAGAAAAGCTTTAAAACTGAAAATGGCACGTGATGTTGGTTGCTGTCGATGTCATT
scd61    ACAAAGCAAACTATAAATACCTATACTATATACATATCTTTGATATATTGTTCTTAATATGATGTGATAGCtTT
scd61    ATTTTAgGGACATCAGAGAAACGGTAGCCTAAGCTCAAAATTAGAGCTTTTTGTAAAAATCAATCCTGTTAATTGC
scd61    TATATAATTATTTCCATTTCTTTTATTCTCTGAtGkYCyymAArkwAmyTCGATGTAACCTTATGTGTAACTTGA
scd61    GTGAATATCACGTTCCTATCCCTCGATTATGCTGCAATAGGAACTTCTGTTTCCAAATGAATCTTGAGATTTTC
scd61    TTCTTTATATAGTATCATATCCTTAGTTTGTA***
```

GAP IN HSCP SEQUENCE

```
                        GTATCGCTTATCAACTTCGTTGCTTCACTTGTTGGAGCTGGTGGTATTCAAGCC
Dm          intron N ---+---------+---------+---------+---------+---------+ 4050
                        V S L I N F V A S L V G A G G I Q A
                                                          III-S4
```

```
         TTCAAGACTATGCGAACGTTAAGAGCACTGAGACCACTACGT
Dm 4051 -+---------+---------+---------+---------+--- no intron
         F K T M R T L R A L R P L R
```

```
HSC 4116+  "Fred"                              TGAGCCCGCATGCAGGGCATG->
HSC 4105-  "Jenny"                             <-ACGTCCCGTACTCCCATGCA
                                                A M S R M Q G M R  intron?
scd72***ATTAGCCGTTCAAAAGCGATGCGAAGCTGGGACTGCGCTCTCAGCCATGAGCCGCATGCAGGGCATGAGGGTACGT
Dm                                              A M S R M Q G M R  intron?
                            GCCATGTCCCGTATGCAGCAGGGCATGAGG
Dm         no intron -------+---------+---------+-------- intron O
                            A M S R M Q G M R
```

FIG. 1M

```
scd72   ACCACCCTGTGCTGCCGACAACACCCTatcgCTCATCATCCACCACACTTCGCTCCACACTTCACATTCACAT
scd72   TTCTATTCAACTTCTACGATCATTTTTAACATTTaAAATTTCCAACGTrCCAGCCGTACTmGGgCTCCTTTTT
scd72   tCGATATTTCTGCATsAATCACCGGATCAAAATTTGTTTTTAATAGTTAATTTGGACAGTTATCCGATTCATTGGC
scd72   AGTAGTCGATTGAAGTAATTATTAGTGAATCATTTTGAAGTGGTCGGTGGCACCCCTGAATGGCTTAGTATCATCA
scd72   CTGTTCGTCATAAACCTCTTTAGAAAGGTCAATGGGATTTATTGTGGAGAGATATTyrTCCATGTtTTGGtCTC
scd72   TTTtCTATTGGTCTTATTATTAGCTAGATTAGACTTTTGTAATTACTTAGTTATTTGGAATGCTAATTTATATTCT
scd72   GCACCTTAGATTTTTCTTCTTGTATCTTCATCGA***
```

GAP IN HSCP SEQUENCE

```
scd131          ***GCTAACTGCTACATAGTTACTGCACAGTATTAATGACA
P20f4/11        ***""""""""""""""""""""A""T"""""""""""""

scd131   TTAACGTCCTTATATCCCAACTAATAATGCGCCCACTAACAAATGCACGCCATTGATATAAGAAAGGAGACGTAT
P20m4/11 ***""""""""""""""""""""""""""""""""""""""""""""""""""""""""""""""""""""""
P20f4/11 """"""""""""""""""""""""""""""""""""""""""""""""""""C"""""""""""""""""""

V   V
scd131   CAGTACTT           CCAATATATCCTTCGTGACCAGTGTAGTAATACGTACGTATGTGACAGGTGGTG
P20m4/11 """"T"GTGGGTACCTACACCCA"""""""""""""""""""""""""""""""""""""""""""""""""
P20f4/11 """""G"             """"""""""""""""""""""""""""""""""""""""""""""""""
Dm                                                                A
                                                                   V   V GTCGTC
                                        intron 0 +----- 4125
                                                   V   V
```

FIG. 1N

```
HSC 4211+          V  N  A  L  V  Q  A  I  P  S  I  F  N  V  L  L  V  C  L  I  F  W  L  I  F          CTGATCTTC...
                   GTAAACGCTCTCGTCGTCAAGGCGATCCCGTCCATCTTCAACGTGTTGTTGGTGTGTCTTATCTTCTGGCTGATCTTC
scd131             """""""""""""""""""""""""""""""A"""""""""""""""""""""""""""""""""""""""""""""
P20m4/11           """""""""""""""""""""""""""""""A"""""""""""""""""""""""""""""""""""""""""""""
P20f4/11
Dm                 GTTAATGCGCTGGTACAAGCTATACCGTCCATCTTCAATGTGCTATTGGTGTCTAATATTTGGCTAATTTTT
          4126     ----+----+----+----+----+----+----+----+----+----+----+----+----+----+ 4200
                   V  N  A  L  V  Q  A  I  P  S  I  F  N  V  L  L  V  C  L  I  F  W  L  I  F
                                                                    III-S5

4211+...GCCATCATGGG->
HSC 4235+ "4215+"           ACAACTGTTCGCTGGmAAATA->
RRO 8+                                          CAAATATTTCAAGGTA          TTAAT->
SSO 8+                                          AAAATATTTCAAGGTAAGCAG->
                             K  Y  F  K
                   A  I  M  G  V  Q  L  F  A  G  K  Y  F  K
scd131             GCCATCATGGAGTACAACTGTTCGCTGGCAAATATTTCAAGGTA          TTAATTTATTAACATAACAAAAA
P20m4/11           """"""""""""""""""""""""""""""""""""""""""""""""""""""""""""""""""""""""G"""""
P20f4/11           """""""""""""""""""""""""""""G"""""""""""""""A""""""""""""""""""C""""T""""""
P1m24/11                                        ***""""""""""""""""A""""""""""""""""""C""""T""""""
Dm                 GCCATAATGGGTGTACAGCTTTTTGCTGAAAATATTTTAAG           AGCAGTA""GT"""C"""""G""""""
          4201     ----+----+----+----+----+----+----+----+----+-- intron P
                   A  I  M  G  V  Q  L  F  A  G  K  Y  F  K HSCO 52-                               <--TAGAATAATCA...
scd131             AATATTTCAATTCGTAAAATCTTATTAGT
P1m24/9            """""""""""""""""""""""""""""
```

FIG. 10

```
                        ...GACAAGTTTA                             C  V  D  L  N  H  T  T  L  S  H
scd131                  GTGTTCAAATTTCTAACATGTTTTCTTGTTCTGTTCTAGTGCGTCGACCTCAACCACGAGACGTTGAGCCAC
P1m24/9                 C"""""""""""""""""""""""""""""""""C""T"""""""""""""""""""""""""""""""""
Dm                                                                TGCGAGGACATGAATGGCACGAAGCTCAGCCAC ---- 4275
                                                                   C  E  D  M  N  G  T  K  L  S  H TGGGAGAACTCACCGATGAACTT->
                                   intron P ------------------------------------>
                             ATCTTAGAGAACTACACCTGGGA->
HSCP4343+
HSC 4325+ (4335+)        E  I  I  P  D  R  N  A  C  I  L  E  N  Y  T  W  E  N  S  P  M  N  F  D  H
scd131                  GAAATCATCCCAGACCGGAATGCTGTGCATCTTAGAGAACTACACCTGGGAGAACTCACCGATGAACTTTGACCAT
P1m24/9                 """""""""""""""""""G"""""A"""""""""""""""""""""""""""""""""""""""""""""""""
Dm                      GAGATCATACCAAATGCCAATCGCAATGCCAATGCCGAGAGCGAGAACTACACGTGGGTGAATTCAGCAATGAATTTCGATCAT
                    4276 ------+---------+---------+---------+---------+---------+---------+ 4350
                         E  I  I  P  N  R  N  A  C  E  S  E  N  Y  T  W  V  N  S  A  M  N  F  D  H <-TCCCTACCTATGTCTAGTAC
HSC 4394- "Heloise"                                                  AGGGATGGATACAGATCATGAA->
HSC 4415+ "4665+"
HSC 4399- "Liz"                                                          <-ACCTATGTCTAGTACTTGCTGCG
                         V  G  K  A  Y  L  C  L  F  Q  V  A  T  F  K  G  W  I  Q  I  M  N  D  A  I
scd131                  GTCGGCAAGGCGTATCTCTGCCTGTTCCAAGTGGCCACCTTCAAGGGATGGATACAGATCATGAACGACGCTATT
P1m24/9                 """""""""""""""""""""""""""""""""""""""""""""""""""""***
Dm                      GTAGTTAACGCGTATCTGTGCCTTTTCCAAGTGGCCACCTTCAAAGGCTGGATACAAATCATGAACGATGCTATC
                    4351 ------+---------+---------+---------+---------+---------+---------+ 4425
                         V  G  N  A  Y  L  C  L  F  Q  V  A  T  F  K  G  W  I  Q  I  M  N  D  A  I
```

FIG. 1P

```
scd131        D  S  R  E
     Dm       GATTCGAGAGAAGTATGGCTACTATTCTTTTCCTTTTGTTCATAAGTTCATAAATTAATATCAATAAAAATATC
       4426   GATTCACGAGAG------ intron Q
              D  S  R  E scd131        ACGCAATACAATAAATGATAT V  G  R  Q  P  I  R  E  T  N  I  Y  M  Y  L  Y  F  V  F  F  I
scd131        TGTTAATGCCAGGTGGGCCGGCAACCTATACGCGAGACGAACATCTACATGTACCTGTACTTCGTGTTCTTCATC
     Dm                   GTGGACAAGCAACCAATTCGTGAAACGAACATCTACATGTACATGCTATTTATATTCGTATTCTTCATC
       4501   intron Q ---+
              V  D  K  Q  P  I  R  E  T  N  I  Y  M  Y  L  Y  F  V  F  F  I
                                                       III-S6

I  F  G  S  F  F  T  L  N  L  F  I  G  V  I  I  D  N  F  N  E  Q  K  K  K
scd131        ATATTTGGCTCATTCTTCACTCTCAACCTATTCATCGGTGTGATCATCGACAACTTTAACGAACAGAAGAAGAAA
     Dm       ATATTTGGATCATTTTTTCACACTCTCAATCTGTTCATTGGTGTTATCATTGATAATTTTAATGAGCAAAAGAAA
       4576                                                                             +4650
              I  F  G  S  F  F  T  L  N  L  F  I  G  V  I  I  D  N  F  N  E  Q  K  K  K A     G  S  L  E  M  F  M  T  E  D  Q  K  K  Y  Y  N    A  M  K  K  M  G  S
scd131        GCC---GGCAGCCTTGAGATGTTCATGACTGAGGACCAGAAGAAATACTACAATGCCATGAAGAAGATGGGTTCT
     Dm       GCAGGTGGATCATTAGAAATGTTCATGACAGAAGATCAGAAGAAGTACTATAGTGCTATGAAAAAGATGGGCTCT
              A  G  G  S  L  E  M  F  M  T  E  D  Q  K  K  Y  Y  S    A  M  K  K  M  G  S
                                          PKC activ'n site West et al Science 254, 866
```

FIG. 1Q

```
         K  K  P  L  K  A  I  P  R  P  K  ?
scd131  AAAAACCTTTAAAAGCTATCCCGAGACCGAAGGTAACAGACGATTGCATTGTTTTTGACCTCAATGAAACA
Dm   4651 ---------+---------+---------+---------+---------+---------+---------+
         AAAAAACCATTAAAAGCCATTCCAAGACCAAGG              intron R
         K  K  P  L  K  A  I  P  R  P  R scd131  TATCCAAGGAGGAGCGAGTCTTATATTTGAAACTTGATAGTAATATTGTTGTATATTTTATAATTCATAAACAG
scd131  CAGTACTGCGGTAAACCATTGTTTTTCAACGCCAGAGACGTTTAATTATTGAGGATGATTTtGCCTA
scd131  GAATCTATTCTAAGATTGATTGGAGCCCGTCCACTTCCAACGACACGTTGAGCATCTATGCCACCGACCACGT
scd131  CGTTGTACCCAGATAAGAAAGCTTTCTACC W  R  P  Q  A  I  V  F  E  I  V  T  D  K
         TAAATAAACACTAACTGAAACTGTTGTTCCAGTGGCGACCACAAGCAATAGTCTTTGAAATAGTAACGATAAG
Dm            intron R      ---------+---------+---------+---------+------ 4725
                                 W  R  P  Q  A  I  V  F  E  L  V  T  D  K
                                                          IV-S1

K  F  D  M  I  I  M  L  F  I  G  L  N  M  L  T  M  T  L  D  H  Y  Q  Q  S
scd131  AAGTTCGACATGATCATCATGTTGTTCATCGGCCTCAACATGTTGACGATGACGCTCGATCACTACCAGTCG
Dm   4726 ---------+---------+---------+---------+---------+---------+---------+ 4800
         AAATTCGATATAATAATCATTATGTTTATTCATTGGTCTCTGAACATGTTCACCATGACCCTCGATCGTTACGATGCGTCG
         K  F  D  I  I  L  M  L  F  I  G  L  N  M  F  T  M  T  L  D  R  Y  D  A  S
```

FIG. IR

```
Q
HSC 4834- (8/10/90)                   <-TACTATAAGTAGCACTATAAGTC
           E  T  F  S     T  V  L  D  Y  L  N  M  I  F  I  V  I  F  S  S  E  C  L  L  K
scd131     GAGACCTTCAGCACTGTCCTCGACTACTTGAACATGATATTCATCGTGATATTCAGTTCAGAGTGCCTATTAAAA
Dm         GACACGTATAACGCGGTCCTAGACTATCTCAATGCGATATTCGTAGTTATTTCAGTTCCGAATGTCTATTAAAA
    4801   ---------+---------+---------+---------+---------+---------+---------+   4875
           D  T  Y  N  A     V  L  D  Y  L  N  A  I  F  V  V  I  F  S  S  E  C  L  L  K
                                   IV-S2

M  F  A  L  R  Y  H  Y  F  V  E  P  W  N  L  F  D  F  V  V  V  N  F  S  I
scd131     ATGTTCGCCTTACGCTACCATTATTTGTTGAGCCATGGAACTTGTTCGATTTCGTAGTAGTCAATTTCTCAATT
Dm         ATATTCGCTTTACGATATCACTATTTTATTGAGCCATGGAACATTTGATGTAGTAGTGTCATTTTATCCATC
    4876   ---------+---------+---------+---------+---------+---------+---------+   4950
           I  F  A  L  R  Y  H  Y  F  F  I  E  P  W  N  L  F  D  V  V  V  V  I  L  S  I
                                                                IV-S3

L  S..
scd131     CTTAGTGAGTATTTGGGTCTCCCTGTTATTCCAATAGTAAAGTGTTTCCATTTATAATTTACTAATGATACACTC
Dm         TTAG
    4951   ---- intron S
           L  G..

SCpu 4991+ (5246+)        T3&AThGArAArTAyTTyGT->
                  ..L  V  L  S  D  I  I  E  K  Y  F  V  S  P  T  L  L  R  V  V  R  V  A
           TCTTTGTTCTCAGTTTGGTATTGAGTGATATATTATAGAAAAATATTTTGTGTCACCCACGTTACTGAGGTGGTGAGAGTAGCG
Dm         GTCTTGTACTTAGCGATATTATCGAGAAGTACTTCGTGTCGCCGACCCTGCTCGTCGAGTGGTGCGTGTGGCG
    intron S ---------+---------+---------+---------+---------+---------+---------+     5025
                 ..L  V  L  S  D  I  I  E  K  Y  F  V  S  P  T  L  L  R  V  V  R  V  A
                                                                IV-S4
R
```

FIG. IS

```
                                                                    TTGTTCGMGCTGGCCAT->
HSC 5097+ (5350+)                                          <-AAGCGGACCGGTACACAGTGA
HSC 5083-                                                                  <-TACAGT....
HSC 5095-
             K  V  G  R  V  L  R  L  V  K  G  A  K  G  I  R  T  L  L  F  G  L  A  M  S
scd131      AAGGTCGGTCGTGTGTTGCGTCTCGTCGTTGCCAAGGGTCGAAGGGTATCCGGACGTTATTGTTCGGGCTGGCCATGTCA
Dm          AAAGTGGGCCGTGTCCTTGACTGGTCGAGGAGCCAAGGGCATTCGGACACTGCTCTTCGGTTGGCCATGTCG
       5026 ----+----+----+----+----+----+----+----+----+----+----+----+----+----+----+ 5100
             K  V  G  R  V  L  R  L  V  K  G  A  K  G  I  R  T  L  L  F  A  L  A  M  S HSC5095-.GACGGTCGGAATAA                                        T3+GCnAThTTyGGnATG->
SCpu 5169+ (5426+)
SCpu 5143- (5430-/5218-)                               <-TACAArTAdAArCGnTA&.M13.-40
             L  P  A  L  F  N  I  C  L  L  L  F  L  V  M  F  I  F  A  I  F  G  M  S  F
scd131      CTGCCAGCCTTATTCAACATCTGTCTGCTGTTCCTTGTGATGTTCATCTTCGCCATCTTCGGCATGTCGTTC
Dm          CTGCCGGCCCTGTTCAACATCTGCCTGCTGCTGTTCCTGGTCATGTTCATCTTCGCCATTTTCGGCATGTCGTTC
       5101 ----+----+----+----+----+----+----+----+----+----+----+----+----+----+----+ 5175
             L  P  A  L  F  N  I  C  L  L  L  F  L  V  M  F  I  F  A  I  F  G  M  S  F
                                 IV-S5

F  M  H  V  K  D  K  G  G  L  D  D  D  V  Y  N  F  K  T  F  V  Q  S  M  I  L
scd131      TTTATGCACGTCAAAGACAAAGGTGGTCTCGACGACGTGTACAACTTCAAGACCTTCGTGCAGAGTATGATCCTG
Dm          TTCATGCACGTGAAGGAGAAGAGCGGCATTAACGACGTCTACAACTTCAAGACCTTTGGCCAGAGCATGATCCTG
       5176 ----+----+----+----+----+----+----+----+----+----+----+----+----+----+----+ 5250
             F  M  H  V  K  E  K  S  G  I  N  D  V  Y  N  F  K  T  F  G  Q  S  M  I  L L  F  Q
scd131      CTATTTCAGGTCAGTGTTACTAATCATACTTTAGCGCCTCCTGGTTGCTTGAGGATGAATGACCACAAGCAACCA
Dm          CTCTTTCAG
       5251 ---------- intron T
             L  F  Q
```

FIG. 1T

```
S                                                                                                              S
scd131      GCAGGGTTTATTCGTTCAAATTGAAAGTTAATTTTAGCCGTTCAAGCATCTAGTGTATGCTAATCTGTCTTATC
Dm          ATCAAACACAGAGTGAGGTTGTTAATTTATGTGTT M   S   T   S   A   G   W   D   G   V   L   D   G   I   I   N   E   E   C   D   L
scd131      GTTTGTCAGATGTCGACGTCNGCGGCTCNGCCGTGGGACTGGAGCGGCATCATCAACGAGGAGTGCGANCTG
                                                                                                        5325
Dm          ATGTCGACGTCAGCCGTCGGATGGTGTACTGACGCGCCATTATCAATGAGGAAGCATGCGATCCA
            intron T +-------+--------+--------+--------+--------+--------+--------+
                        M   S   T   S   A   G   W   D   G   V   L   D   A   I   I   N   E   E   A   C   D   P P   D   N   E   R   G   Y   P   G   N   C   G   S   A   T   I   G   I   T   Y   L   L   S   Y   L
scd131      CCGGACAACGAGCGCGGCTACCCCGGCAACTGCGGCTCTGCNACCATGGCATCACCTACCTGTCCTACCTC
                                                                                                        5400
Dm  5326    CCCGACAACGACAAAGGCTATCCGGGCAATGTGGTTCAGGCGCCGTTCAGCAGCGACCGTTGAATAACGTTTCTCCTCTACCTA
            +-------+--------+--------+--------+--------+--------+--------+--------+
                        P   D   N   D   K   G   Y   P   G   N   C   G   S   A   T   V   G   I   T   F   L   L   S   Y   L
                                                                                IV-S6

SCpu 5425- (5712-)         <--TTrTACATrTAdCGnCAgagtgaccggcagcaaa                      V   I   L   E   N   Y   S   Q   A   S   *
scd131      GTCATCTCCTTCCTCATCGTCATCAACATGTACATCGCCGTCATTCTCGAGAATTACTCGCAGGCAAGTTGA
                                                                                                        5461
Dm  5401    GTTATAAGCTTTTTGATAGTTATTAATATGTACATTGCTGTGTATCTTGAGAACGGAATTC
            +-------+--------+--------+--------+--------+--------+
                        V   I   S   F   L   I   V   I   N   M   Y   I   A   V   I   L   E   N   G   I
```

METHOD FOR MONITORING PESTICIDE RESISTANCE

Each year, approximately one third of the world's crops are destroyed by plant pests, amounting to billions of dollars in crop losses in the United States alone. Plants are susceptible to diseases and damage caused by an enormous number of different types of organisms, including virus, bacteria, fungi, algae, parasitic plants, weeds, insects, arachnids, and nematodes. The potential losses are kept in check by natural controlling mechanisms, and when these systems fail, by applications of various types of insecticides which typically act by attacking one specific, genetically controlled aspect of the target organism's metabolism. However, the efficacy of any given pesticide may be limited by the appearance and spread of resistance to the pesticide among the target population. The appearance and spread of insecticide resistance in wild populations argues for a genetic origin. First, a resistant genotype or trait appears in a local population and then with continued insecticide use (and thus, disproportionate survival of individuals with this genotype or trait), the resistance rapidly increases in the population and via migration resistance may spread to regional and perhaps even worldwide populations. Resistance may arise as a genetic allele already present within a population, or it may arise de novo. Nonetheless, whatever the cause, in a population with a short generation time (which is characteristic of many insects), the resistance trait can spread rapidly and quickly render ineffective the planned pattern of pesticide application.

The continued development of natural strategies for insect control could be enhanced by an understanding of the genetic basis of the resistance in economically important pests. Such studies have been ongoing, particularly with regard to insect pests, and a great deal has been learned about the major types of resistance observed in insects. At least three types of insect resistance have been identified: decreased rate of uptake, increased rate or degradation and changes in the target site. To some extent, certain aspects of the genetic mechanisms of these types of resistance have been determined; however, knowledge of the specific genetic basis for resistance has not yet been effectively applied in the field to monitor the occurrence of resistance, or to assist in planning effective insecticide applications to avoid or alleviate the development of resistance. Modification of insecticide application patterns can be critical in cases in which resistant insects are otherwise less fit than non-resistant insects; application of insecticide to which some individuals are resistant in these cases may actually select for increase in resistance in the population, when it might otherwise have been maintained only at low levels or entirely eliminated from the population. Thus, a method for exploiting the available knowledge of the genetic basis for resistance is greatly needed.

Some of the most destructive of insect pests are found among the order Lepidoptera. The damage caused by lepidopterans is most frequently related to feeding activity of their larvae (caterpillars) on plants. Of the lepidopteran plant pests, among the most damaging are those insects related to the genus Heliothis. Two species of the genus Heliothis, *H. virescens* (the tobacco budworm) and *H. armigera* (American bollworm), and *Helicoverpa zea* (the corn ear worm) are responsible for the tremendous amount of damage to tobacco, cotton, corn, beans, alfalfa, and solanaceous plants in the United States. Over the years these pests have been controlled by application of a variety of insecticides; however, *H. virescens* has regularly developed resistance to compounds from virtually every major insecticide class. As one exception, until fairly recently the pyrethyroid class of insecticides continued to effectively control Heliothis in the field. Unfortunately, it has recently been noted that pockets of tolerance or resistance are beginning to appear in *Heliothis virescens* populations in various areas in the United States and in *H. armigera* and *H. punctigera* abroad. Because pyrethroids represent the most effective control of these insects, it is essential that widespread occurrence and/or spread of resistance to pyrethroids be avoided.

Resistance to pyrethroids has been extensively studied in a variety of dipterans, and a number of different patterns of inheritance and explanations for resistance have been suggested. However, the basis for pyrethroid resistance or tolerance in lepidopterans generally, and in Heliothis specifically, has not yet been clarified. An understanding of the genetic mechanism of resistance, or even a definable genetic marker for resistance, would provide a much-needed basis for tracking the resistance trait accurately in a population. The present invention now provides the necessary tools for monitoring the occurrence and spread of resistance in a population, in particular for pyrethroid resistance in lepidopteran populations.

SUMMARY OF THE INVENTION

The present invention provides an isolated nucleic acid fragment encoding all or a portion of a non-dipteran sodium channel. This channel is believed to be target site for sensitivity to a variety of different insecticides, including pyrethroids, and is useful as a marker for such target-insensitive insecticide resistance. Preferably the fragment encodes a lepidopteran, coleopteran or homopteran sodium channel. Sodium channels from both resistant and sensitive strains are encompassed herein. The nucleic acid fragment provides the basis for probes useful in detecting the presence of the resistance trait in a population of insects to be evaluated. Also provided are vectors containing the resistance gene which may be used to introduce a gene encoding insecticide resistance into beneficial insects, such as honey bees. The invention also provides the isolated protein or fragment encoded thereby, as well as biologically or immunologically active fragments thereof, which protein or fragments are useful in generation of polyclonal and monoclonal antibodies. Such antibodies can be used to detect the presence of sensitive or insensitive sodium channels. In a preferred embodiment, the insecticide target is a Heliothis sodium channel.

The invention also provides a means for monitoring, both quantitatively and qualitatively, the level of resistance in any given pesticide target population. The presence or absence of a resistance trait is determined by hybridizing whole genomic DNA, cDNA or one or more restriction fragments from one or more individuals from the population with a nucleic acid probe based on the sequence of a nucleic acid encoding a pesticide target site. Quantification of the trait is further obtained by calculating the number of the individuals having resistance relative to the number of sensitive individuals, and calculating the percentage occurrence of resistance. This in turn permits the observer to determine whether or not the contemplated pesticide application will be effective, whether alternate treatment may be required, or to predict when, at some time in the future, alternate treatment may be needed. In an alternate embodiment, the DNA can be used to express a recombinant protein or peptide, which in turn can be used to raise monoclonal antisera. Preferably antisera that can specify or identify both resistant and sensitive targets are raised. Such monoclonal antibodies may then be utilized in routine immunological procedures to determine the presence or absence of the resistant protein in a population.

The present invention also provides the basis for an in vitro screen which will detect potential insecticidal activity. A nucleic acid sequence encoding a lepidopteran sodium channel can be inserted into a convenient host cell and a battery of potential insecticides tested for their ability to interfere with expression of either the gene or the encoded protein.

DETAILED DESCRIPTION OF THE INVENTION

As described in detail in the following Examples, the Heliothis sodium channel is isolated by amplification of Heliothis genomic DNA from an inbred susceptible strain using degenerate primers homologous to a portion of a sodium channel gene from *Drosophila melanogaster* (Loughney et al. Cell 58:1143–1154, 1989), as described in Example 2. A 184 bp amplification product is obtained which, upon sequencing, is found to encode an identical amino acid sequence when compared to the same region in the Drosophila gene. This PCR product is then labelled and hybridized to restriction enzyme-digested Heliothis genomic DNA. The highest molecular weight DNA fragment identified is from an EcoRI digest.

Genomic DNA is then isolated from a resistant Heliothis strain and digested to completion with EcoRI. A genomic library is constructed in a g Zap II vector, and a labelled 184 bp fragment is then used to screen this library. One positive plaque yields a genomic clone of approximately 8000 bp which is referred to as "hscp1." This clone shows significant homology to the published Drosophila sequence (FIG. 1).

Figure 1H:
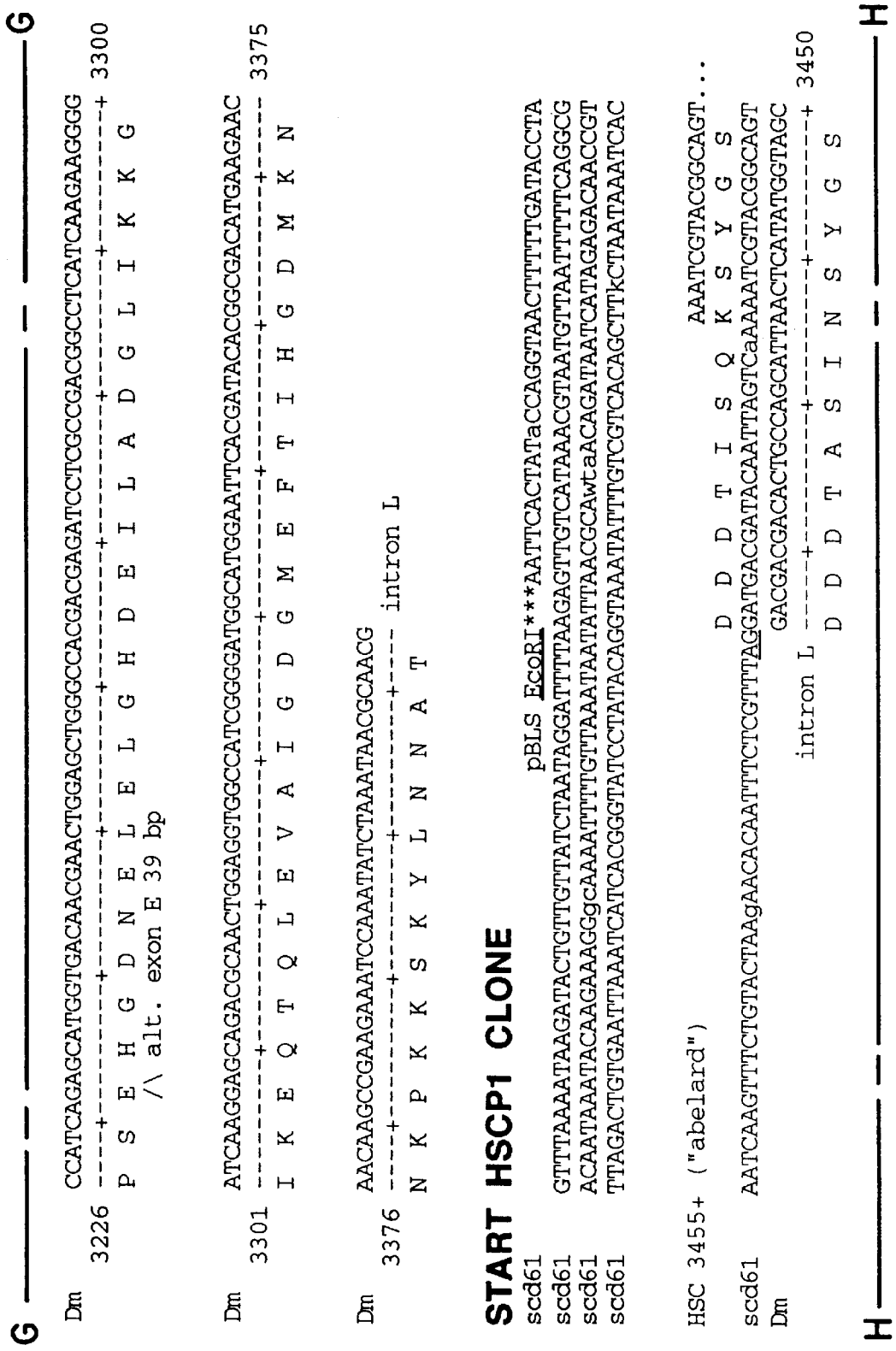
FIG. 1 illustrates the nucleotide and amino acid sequences of the Heliothis clone hscp1, in comparison with the nucleotide and amino acid sequence of the para locus (sodium channel) of Drosophila melanogaster. "Dm"=Drosophila sequence; "scd"=portions of the Heliothis sequence; the numbers after "scd" refer to various subclones used to determine the sequence. For example, scd61 (SEQ ID NO:1), scd72 (SEQ ID NO:2), and scd131 (SEQ ID NO:3) are shown. The predicted amino acid sequences encoded by scd 61, scd 72, and scd 131 correspond to SEQ ID NO:4, SEQ ID NO:5, and SEQ ID NO:6, respectively. The DNA and amino acid sequences of the Drosophila para locus ("Dm") correspond to SEQ ID NO:7 and SEQ ID NO:8, respectively. The underlined amino acid sequences are membrane-spanning domains of the sodium channel. Superimposed above the sequences are the specific sequences of various primers (e.g. HSC 3455+) used in cloning and/or sequencing procedures including those designated SCp788+ (SEQ ID NO:11); D&K+ (SEQ ID NO:12); SCp1153– (SEQ ID NO:13); D&K– (SEQ ID NO:14); HSC3455+ (SEQ ID NO:15); HSCP3868– (SEQ ID NO:16); SCp3975+ (SEQ ID NO:17); HSC4116+ (SEQ ID NO:18); HSC4105– (SEQ ID NO:19); HSC4211+ (SEQ ID NO:20); HSC4235+ (SEQ ID NO:21); RRO8+ (SEQ ID NO:22); SSO3+ (SEQ ID NO:23); HSC052– (SEQ ID NO:24); HSCP4343+ (SEQ ID NO:25); HSC 4325+ (SEQ ID NO:26); HSC4394– (SEQ ID NO:27); HSC4415+ (SEQ ID NO:28); HSC4399– (SEQ ID NO:29); HSC4834+ (SEQ ID NO:30); SCpu4991+ (SEQ ID NO:31); HSC5097+ (SEQ ID NO:32); HSC5083– (SEQ ID NO:33); HSC5095– (SEQ ID NO:34); SCpu5169+ (SEQ ID NO:35); SCpu5143– (SEQ ID NO:36); SCpu5285+ (SEQ ID NO:37); and SCpu5425– (SEQ ID NO:38). Numbering is based on the Drosophila homologue sequence to the Heliothis sodium channel.
Figure 2:
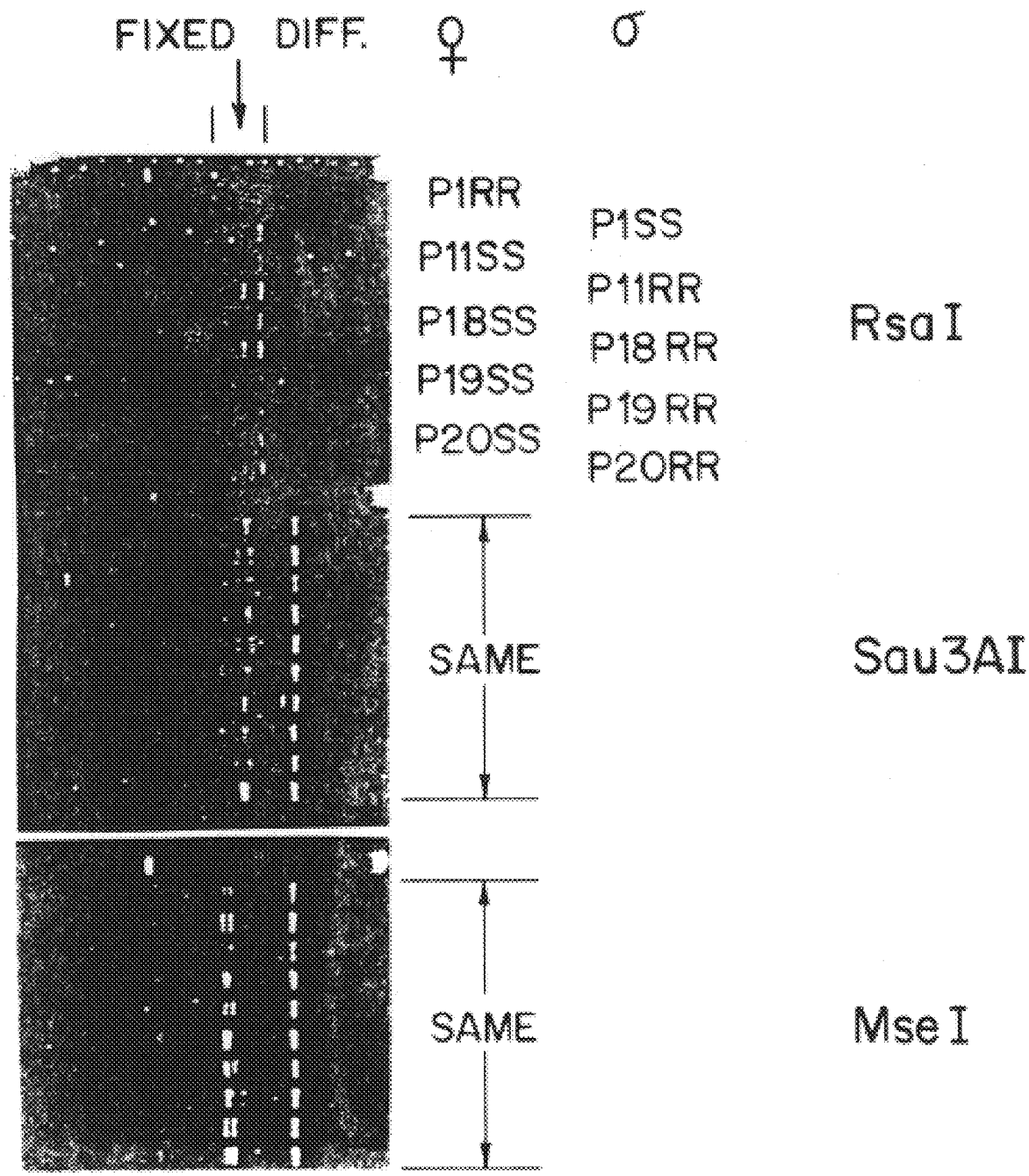
FIG. 2 shows Restriction Fragment Length Polymorphisms (RFLPs) developed utilizing a labelled hcsp1 DNA sequence as a probe. "RR" identifies DNA derived from resistant individuals and "SS" refers to DNA derived from sensitive individuals. The presence or absence or resistant and sensitive individuals is made by the vial test described by Campanhola and Plapp, *J. Econ. Entomol.*, 82:1577–1533, 1989. Protocols for the procedure are described in Example 3.

Based on the hspc 1 sequence, a pair of primers designated 4116+, and 4399– (as depicted in FIG. 1) are used to amplify fragments of the sodium channel gene from both resistant and susceptible Heliothis individuals. Fragments are digested with either RsaI, Bau3AI or MseI. The restriction fragments are then separated and analyzed by gel electrophoresis. The resulting Restriction Fragment Length Polymorphisms (RFLPs) show distinct patterns unique to resistant and susceptible individuals. This demonstrates the utility of a nucleic acid sequence for defining genetic RFLP patterns useful for identifying resistant individuals within a population (FIG. 2).

By homology with the known nucleic acid sequence for a Drosophila sodium channel, it is presumed that the isolated Heliothis sequence represents a portion of the corresponding Heliothis channel. Also, by comparison with the available information regarding the Drosophila channel as being the target site of pyrethroid action, it is reasonable to extrapolate this function in Heliothis as well. However, whether or not the isolated sequence represents the target site, or a genetic locus that is tightly linked with resistance, the RFLP results described above show that different in the DNA is a reliable marker for identifying differences in susceptibility to insecticides that primarily target the sodium channel, particularly pyrethroids (but also chlorinated hydrocarbons and venom components such as the toxin derived from *Androctonus australis* [AaIt], saxitoxin, tetrodotoxin and the like) in the insect population.

The isolation of the DNA sequence encoding the Heliothis sodium channel provides a number of advantages. First, in view of the unexpected high level of homology between Drosophila and Heliothis sodium channels, it must be assumed that channels of other lepidopteran species have similar or even higher homology to the Heliothis sodium channel. Thus, the Heliothis sodium channel DNA provides the basis for isolation of other lepidopteran channels. Such lepidopteran channels can be readily isolated by hybridization under medium (e.g., 1×SSC, 0.1% SDS, 55° C.) or high (0.1×SSC, 0.1% SDS, 65° C.) stringency conditions using the Heliothis DNA or portion thereof, to function as an identifiable probe when screened against cDNA or whole genomic libraries from the species of interest. Isolation of DNA hybridizing under said conditions can be achieved by standard techniques. Lepidopteran species of interest include, but are not limited to: other Heliothis species, such as the American bollworm, *H. armigera* and the bollworm, *H. punctigera;* lepidopteran species of the genus Spodoptera, e.g., the Egyptian cotton leafworm, *S. litteralis*, the best armyworm, *S. exigua;* the fall armyworm, *S. frugiperda;* the cutworm, *S. litura*, the rice swarming caterpillar, *S. mauritania* and the Southern armyworm, *S. eridania;* and other miscellaneous lepidopterans, e.g., the pink bollworm, *Pectinophora gossypiella;* the spiny bollworm, *Earius insulana,* the cotton leafworm, *Alabama argillacea;* the leaf perforator, *Bucculatrix thurberiella;* the tomato fruitworm, *Helicoverpa zea;* the diamondback moth, *Plutella xylostella;* the cabbage looper, *Trichoplasia ni;* the imported cabbageworm, *Artogeia rapae;* the imported cabbageworms *Hellula undalis* and *Hellula rogatalis;* the black cutworm, *Agrotis ipsilon;* the corn earworm, *Ostrinia nubalis;* the tomato pinworm, *Keiferea lycopersicella;* the tomato hornworn, *Manduca sexta* and *Manduca quinquemaculata;* the velvet bean caterpillar, *Anticarsia gemmatalis;* the green oliveworm, *Plathypena scabra;* the soybean looper, *Pseudoplusia includens;* the saltmarsh caterpillar, *Estigmene acreas;* the leaf miner, *Epinotia meritana;* the codling moth, *Cydia pomonella;* the oblique banded leafroller, *Choristoneura rosaceana;* grape berry moth, *Lobesia botrans;* currant tortrix, *Pandemis cerasana;* spotted tentiform leafminer, *Phyllonocytes blancardella;* grape leafroller *Sparganothis pilleriana;* tufted bud apple moth, *Platynota idacusalis;* red banded leafroller, *Argyrotaenea valutinana;* oriental fruit moth, *Grapholitha molesta;* Southwestern corn borer, *Diatraea grandiosella;* rice leafrollers, *Cnaphalocrocis medinalis, Marasmia exigua* and *Marasmia patnalis;* striped borer, *Chilo suppressalis;* dark headed stem-borer, *Chilo polychrysis;* yellow stem borer, *Scirophaga incatulas;* white stem borer, *Scirophaga innotata;* and pink stem borer, *Sesamia inferens.*

The isolated Heliothis nucleic acid fragment is also useful in other regards. The newly observed homology between Drosophila and Heliothis sodium channels predicts not only substantial homologies between Heliothis channels and other lepidopteran species, but also between Heliothis and other non-lepidopteran insect channels. Thus, the fragment, or portions thereof, can be utilized in developing RFLP's for other lepidopteran species, including, but not limited to, e.g., the lepidopteran species noted above, as well as non-lepidopteran species such as as the Colorado potato beetle *Leptinotarsa decimlineator,* the boll weevil, *Anthonomus grandis;* the Southern corn rootworm, *Diabrotica undecimpunctata;* the Japanese beetle, *Popillia japonica;* plum curculio, *Conotrachelus nenuphar;* brown planthopper, *Nilaparvata lugens;* green leafhopper, *Nephotettix virescens;* potato leafhopper, *Empoasca abrupta;* cotton sphid, *Aphis gossypii;* green peach aphid, *Myzus persicae;* sweet-potato whitefly, *Bemisia tabaci;* imported fireant, *Solenopsis invicta;* thrips, e.g., *Thrips palini;* pear psylla, *Psylla pyri;* two-spotted spider mite, *Tetranychus urticae;* carmine mite, *Tetranychus cinnabarinus;* citrus rust mite, *Phyllocoptruta oleivora;* German cockroach, *Blatella germanica;* cat flea, *Ctenocephatides felis;* yellow fever mosquito, *Aedes aegypti;* and salt marsh mosquito, *Aedes sollicitans.* The generation of useful RFLPs for these species is achieved in substantially the same manner as described herein for Heliothis.

The Heliothis nucleic acid fragment or portions thereof can also be used as a probe, or can be used as the basis for designing degenerate probes, to screen genomic or cDNA libraries derived from such other non-lepidopteran insect species for specific sodium channels from these species. However, given the herein demonstrated high level of homology between the distantly related Drosophila and Heliothis, it is quite likely that the present *Heliothis virescens* fragment can be used directly as a probe for identifying resistant sodium channels by RFLPs for other lepidopteran and nonlepidopteran species, without the need for isolation of these species' specific sodium channel DNA fragments.

Continued monitoring and early detection of the presence of a resistance trait in any population is essential to effective insect control. By the time resistance is apparent at the gross level, it is very likely already at a point where further treatment with the pesticide is doomed to failure. For example, application of pyrethroids to a population in which resistance is already established will substantially increase the selection pressure favoring the appearance of the resistant trait. Whereas, in the absence of such selection, the resistant individuals are reproductively less fit than sensitive (wild-type) individuals. Hence, resistance would not otherwise have become established in the population without the application of insecticides. Thus, selective and timely application of pesticides or recognition of need for alternative application of pesticides at an early stage can be critical in maintaining suitably sensitive insect populations.

The identification of a genetic trait associated with resistance provides several avenues for tests to monitor the occurrence and frequency of resistance in a population at a very early stage, when frequency may be low and/or undetectable by standard bioassays. Early observance permits for informed judgments in the application of the relevant pesticide. For example, the gene encoding the resistant sodium channel provides the basis for informative southern or RFLP analysis of an insect population to identify the presence of the resistance trait in a given population. Detection of the unique DNA associated with a resistance allele (or the presence of two distinct alleles) therefore is diagnostic for the presence of the resistance trait in an analyzed sample. This may be determined, for example, by digesting genomic DNA collected from individuals of the target population in question and probing a Southern blot with detectably labelled DNA sequence that identifies a particular resistance trait, or a diagnostic portion thereof, to identify the presence or absence of the resistance allele. By "diagnostic portion" thereof is meant any fragment of the hscp1 DNA which differs sufficiently in sequence form the corresponding portion of the susceptible DNA sequence, or a unique DNA sequence genetically linked to the trait, so as to assure its hybridization, under high stringency conditions, only with DNA encoding the resistance trait. It should be noted that sequences flanking the resistance gene, as well as intervening sequences (introns) are particularly suited for identifying unique diagnostic RFLPs.

RFLP analysis also provides an attractive method of analyzing the existence and frequency of the resistance trait in the population. As the Examples below show, there is a detectable polymorphism associated with the sodium channel DNA between resistant and susceptible individuals. Thus, target population DNA can be analyzed for the presence of polymorphisms using the detectably labelled cloned hscp1 DNA as a probe. In this technique, DNA from several individuals in the target population is digested with an appropriate restriction enzyme, and size separated by gel electrophoresis. The gel, or a blot derived therefrom, is then probed with labelled DNA, either the whole gene or fragment. If there are both resistant and sensitive alleles within an individual in the population, there will appear on the gel two different sized restriction fragments, each of which will hybridize with the hscp1 probe. In this manner, large numbers of individuals in the population can be sampled, and the relative abundance of the allele can be determined. Identification of the specific DNA fragment associated with resistance, whether by Southern or RFLP analysis, will always be diagnostic.

In this regard, the present invention also provides a kit for evaluating the extent to which a resistance gene is present in a given population. The kit will contain as its principle components (1) a restriction enzyme for digesting DNA, and (2) a detectably labelled probe comprising a nucleic acid fragment capable of hybridizing specifically with DNA encoding the resistance trait, or a nucleic acid fragment capable of hybridizing with the diagnostic RFLP marker. In a preferred embodiment, the kit also comprises (3) a means for extracting DNA from cells of the target population, and/or (4) PCR primers useful in amplifying the target DNA sequences. Also included may be a set of reference standards comprising sensitive and resistant DNA.

As a specific example, a kit for the detection of altered sodium channels in a population would include (1) a restriction enzyme such as TaqI or EcoRI, which will generate fragments which show the relevant polymorphism, if present (2) a radioisotope- or biotin-labelled DNA comprising the sequence of the sodium channel or fragments thereof; and optionally (3) a DNA extraction means.

It will be recognized by those skilled in the art that variations or components (1) and (2) in particular are contemplated. Any restriction enzyme which produces a detectable polymorphism can be used. Preferably, the enzyme used will be a 4-cutter, such as Sau96I, ScrFI, Sau3A1, RsaI, MseI, MspI, MboI, HpaII, HinPI, HaeIII, DpnII, BstVI, and BfaI; or a 6-cutter, such as EcoRI, BamHI, HindIII, PstI, and SalI; less useful are 8-cutters, such as NotI, StoI, PacI, Sse36I, AscI, FseI, PmeI, RsrII, or SwaI. The utility of any given restriction enzyme can readily be determined by digesting DNA known to contain alleles for both resistance and sensitivity with the candidate enzyme, and observing the presence or absence of a polymorphism by probing with hscp1, or any DNA linked to this region. Also, it will be understood that the "detectably labelled" DNA may alternately be labelled so as to be detectable in any manner known in the art, e.g., by chemiluminescence, bioluminescencse, ELISA, biotin-avidin, or any other appropriate means. The foregoing scheme is useful for detecting the presence of resistance to not only pyrethroids, but also DDT and arthropod toxins, such as the sodium channel toxin derived from *Androctonus australis* (AaIT).

Those skilled in the art will also recognize that the approach to resistant pest management described herein is not limited solely to control of resistance based on an altered sodium channel. Utilizing target site DNA as a means of tracking the presence of resistance in a population provides a far more precise and sensitive measure of the prevalence of resistance than do previously utilized methods. The target sites for many types of pesticides are now known, and therefore, the proposed genetic analysis for a resistance trait can be applied to other insecticides as well. For example, acetylcholinesterase is known to be the target site for carbamate and organophosphate insecticides (Oakeshott et al., PNAS USA 84:3359–3363, 1987). Organophosphate insecticides include malathion, methylparathion, diazinon, turbophos and dicrotophos; carbamates include sevin, Aldicarb, methionyl and thiodicarb. Target site resistance to some of these insecticides has been reported (Karunaratre et al., Resist. Pest. Manag. Newsletter, 3:11–13, 1991; Chen, Resist. Pest Manag. Newsletter, 2:15, 1990). The acetylcholinesterase gene has been cloned (Fournier et al., J. Mol. Biol. 210:15–22, 1989), providing the basis for development of an analogous detection system for this type of resistance. Monooxygenase and mixed function oxidases (MFOs) have also been shown to be involved in resistance by increase in the rate of metabolism of organophosphates and carbamates (Brattstein et al., Science, 1961349–1352, 1977; Brattstein et al., Pesticide Biochem. Physiol., 3:393, 1973, Krieger et al., Science, 172:579, 1971; Matsumara, Toxicology Insecticides, Plenum Press, New York, 1975). Cyclodienes have been shown to act at the GABA receptor (Kadous et al., Pestic. Biochem. Physiol. 19:157–166, 1983; Tanaka et al., *Pestic. Biochem. Physiol.*, 22:117–127, 1984); and target site resistance is known to exist (ffrench-Constant et al., J. Econ. Entomol. 83:1733–1737, 1990) and the receptor gene has been cloned (french-Constant et al., PNAS USA, 88:7209–7213, 1991). Similarly, methoprene and certain botanical extracts (Precocenes) target the juvenile hormone (JH) receptor and resistance to these insecticides has been reported (Wilson et al., Develo. Biol., 118:190–201, 1986; Georghiou et al., J. Econ. Entomol., 71:544–547, 1978; Dyte, Nature, 238:48–49, 1972). *Bacillus thuringiensis* (Bt) toxins affect a gut associated glycoprotein but resistance has not become widespread. Diacyl hydrazine and certain botanical extracts (Penosterone A) target the ecdysone receptor (Wing, Science, 241:467–469, 1988; Spindler-Barth et al., Arch. Ins. Biochem. and Phys., 16:11–18, 1991; Cherbas et al., PNAS USA, 85:2096–2100, 1988) and the genes for the ecdysone receptor have also been cloned (Yao et al., Cell, 71:63–72, 1992; Koelle et al., Cell, 67:59–77, 1991).

The use of this method is also not limited to detection of insecticide resistance, but may be applied to any other pesticides, including herbicides, acaricides, fungicides, nematicides, and molluscicides. A number of genes conferring resistance to herbicides have been characterized. For example, altered acetohydroxy acid synthase genes are the basis of resistance to sulfonylureas and imidazolinone herbicides (EP Application No. 91 119 254.0; Yadav et al., PNAS USA 83:4418–4422, 1986). Glyphosate targets the enzyme 5-enolpyruvate shikimate-3-phosphoric acid synthase, and mutant genes encoding resistant forms of this enzymes have been identified (Comai et al., *J. Biol. Chem.*, 260:4724–4728, 1985). Similarly, genes conferring resistance to the herbicides phosphothrinicin and bialyphos have also been characterized (Thompson et al., *EMBO J*, 6:2519–2523, 1987; DasSarma et al., Science, 232:1242–1244, 1986).

The target site of various fungicides is also known. For example, phenylamide fungicides, such as acylalanines (metalaxyl, furaxyl and bevalaxyl), butrolactones (ofurase, cyprofuran), and oxazolidinones (oxadixyl) are known to act on fungal RNA polymerase (Arp et al., Fingizider. Mitt. Biol. Bundesanst 236–237, 1981; Davidse, Neth. J. Plant Pathol. 87:11–24, 1981; EPPO Bull 15:403–409, 1985). Resistance to these fungicides has also been reported (Davidse et al., J. Plant Pathol., 87:65–68, 1981; Davidse et al., Experiment. Mycology, 7:344–361, 1983). The fungicide carboxin is known to have as a target site succinate dehydrogenase (Schewe et al., in Modern Selective Fungicides, H. Lyr, ed. V. E. B. Gustan Fischer Vertag. Jene, 1987). Resistance and cloning of the resistance gene have also been reported (Keon et al., Current Genetics, 19:475–481, 1991). The blasticidin fungicides, such as BlaS and Blasticidin S act on the enzyme nucleoside aminohydrolase; resistance has been observed and the gene conferring the resistance has been cloned (Kamakura et al., Mol. Gen Genet. 223:169–179, 1990; Kamakura et al., Agric. Biol. Chem., 51:3165–3168, 1987). The benzamidazole fungicides, such as benemyl, carbendazin, mocodazole and thiabenazole, act by affecting with microtubule function (Clemons et al., Pesticide Biochem. Physiol., 1:32–43, 1971; Hammersdag et al., Pesticide Biochem. Physiol., 3:42–54, 1973). Resistance is also known to occur to these fungicides (Van Tuyl, Med. Fac. Lonbouww Ryksuniv. Gent., 40:691–698, 1975); Meded. Landb. Hogesch. Wageningen, 77:1–137, 1977); Fanetran et al., Mycol. Res., 95:943–951, 1991). The relevant resistance gene has been isolated and cloned (Jang et al., Cell Motility and the Cytoskeleton, 17:87–94, 19906; Orbach et al., Mol. Cell Biol., 6:2452–2461, 1986).

Other applications of this method will be apparent to those skilled in the art, in view of the following non-limiting examples.

EXAMPLES

1. DNA Preparation

Genomic DNA is prepared from adults of an inbred American Cyanamid Company susceptible strain of *Heliothis virescens* as follows. A moth is placed in 400 ml of grinding buffer (0.1 M Tris-HCl, pH 9.0, 0.1 M EDTA, 1% SDS) and homogenized with a pestle. 80 ml of 5M KOAc and 400 ml equilibrated phenol is added; the sample is inverted several times and left to stand on ice for five minutes. Two hundred ml of ice cold chloroform is added, spun at 15,000×g for five minutes, and supernatant removed. The procedure is repeated at least once.

Four hundred ul chloroform is added to the pellet, the sample inverted for 30 seconds and then spun for 5 minutes at 15,000×g. The chloroform is removed, the sample spun again for one minute and the remaining chloroform removed. Two volumes of cold ethanol are added to the aqueous phase, and the sample left to stand five minutes at room temperature. The sample is once again spun for five minutes, the supernatant aspirated, and the pellet dried. The dried pellet is resuspended in 50 ul Tris-EDTA (10 mM TRIS, 1 mM EDTA, pH 8.0).

2. Isolation of Channel Fragment from Genomic DNA

The isolated genomic DNA is used as a template in PCR with primers based on portions of the *Drosophila melanogaster para* locus sodium channel.

Specifically, degenerate primers homologous to portions of an exon in the fourth transmembrane domain of the a-subunit of the *Drosophila para* locus are constructed as follows:

| | | |
|---|---|---|
| para 4991+ | 5' (T3) <u>GAAATCACTCCCAATTA</u> ATH GAR AAR TAY TTY GT 3' | SEQ ID NO:39 |
| para 5143- | 5' (M13-40) <u>TTTCCCAGTCACGAC</u> ATN GCR AAD ATR AAC AT 3' | SEQ ID NO:40 | where H=A, C or T, R=A, G or T, Y=C or T, and N=any base. Numbers refer to 3' terminal base positions in the para sequence. Underlined sequences are universal primer tails T3 and M13–40 respectively used for sequencing of product.

PCR reactions of 100 ul are constructed of approximately 1 mg of genomic CNA, 1 mg of each primer, 0.2 mM of each dNTP, 10 mM Tris pH 8.3, 50 mM KCl, 2 mM $MgCl_2$, 0.001% gelatin, and 2 U of Taq polymerase. Reactions are incubated for 5 cycles, each of 50 seconds at 94° C., 2 minutes at an annealing temperature of 53° C., and 25 seconds at 72° C., then for 35 cycles with an annealing temperature of 45° C. An amplification product of 184 base pairs is obtained, and then directly sequenced using the Sequenase kit (United States Biochemical Co.) according to the manufacturers directions. The deduced amino acid sequence is found to be the same as for an equivalent region in para.

Genomic DNA is also digested with several restriction enzymes, specifically EcoRI, BamHI, BalI, HindIII, PstI, and XbaI. The fragments are separated on agarose gel and transferred to a nylon support. The PCR product described above is radiolabelled and hybridized to the nylon blot at 60° C. overnight. The blot is washed with a wash buffer (lMNaPi, 250 mM EDTA, pH , 20% SDS; Napi= $Na_2HPO{\cdot}7H_2O$, 134 g and $H_3PO_4$ to pH 7.2/liter) at 60° C. three times for thirty minutes each. The filter is exposed to film. The film is developed after 12–24 hours of exposure at −80° C. The results show single bands in each lane indicative of a single copy gene. The largest band is for the EcoRI digest.

Based on the foregoing information genomic DNA is prepared from an ICI America's pyrethroid resistant PEG-87 *H. virescens* strain using cesium chloride purification as described by Ausubel et al. (Current Protocols in Molecular Biology, Green Publ. Assn. and Wiley Interscience, 1989), and digested to completion with EcoRI. This DNA is used to construct a genomic library in the Lambda-ZapII vector (Stratagene Co., LaJolla, Calif.) following manufacturers' instructions. The 184 bp PCR fragment is used to screen this library by hybridization as described in standard Lambda-Zap II protocols. Several positive plaques are purified and the inserts excised in vitro following manufacturer's instructions, and subsequently characterized. A genomic clone designated "hscp1" has approximately 8000 bp, and is extensively sequenced. For this first 990 base pairs of coding sequence, there is significant homology between hscp1 and the published para sequence of Drosophila (Loughney et al., *Cell,* 58:1143–1154, 1989).

3. RFLP Analysis

Fragments of the gene from individuals of both ICI-pyrethroid-resistant lines and American Cyanamid Company susceptible strains (collected Stoneville, Miss., 1963) are amplified by PCR using several pairs of primers based on the available hscp1 sequence. In this specific example, hscp4116+ and hscp4399− are used. The PCR reactions, of 100 ml, consist of 100 ng-1 mg of genomic DNA, 100 ng each of primer (hscp 4116+, 4399−, as shown in FIG. 1) and other components as described above. Negative and positive control reactions are also made respectively, without template DNA or with hscp1 DNA.

Reactions are incubated for 30 cycles, each of 50 seconds at 94° C., 2 minutes at an annealing temperature of 56° C., and 1.5 minutes at 72° C. PCR products are purified with phenol, chloroform and precipitated using ammonium acetate-ETOH. PCR products are then apportioned among three different restriction enzyme reactions mixes following manufacturers' instructions (RsaI, Sau3AI, and MseI, New England Biolabs, Beverly, Mass.), and incubated at 37° C. overnight. Digestion products are resolved on a 3% "NuSieve" (FMC) agarose gel and stained with ethidium bromide at about 50 ng/ml. The resulting restriction fragments length polymorphisms show a distinct pattern for each of the resistant and susceptible strains (FIG. 2), indicating the utility of this method in detecting the presence of resistant individuals among a generally susceptible population.

DEPOSIT OF BIOLOGICAL MATERIALS

The following materials have been deposited with the American Type Culture Collection, 12301 Parklawn Drive, Rockville, Md., on Oct. 19, 1992 and have been given the following accession numbers.

| Deposit | Accession No. |
|---|---|
| Sodium channel para homolog (3' half of gene) from *Heliothis virescens* ICI strain PEG-87 (hscp1) | ATCC 75334 |

What we claim is:

1. An isolated nucleic acid sequence consisting of the Heliothis sequence as set forth in SEQ ID NO:1, SEQ ID NO:2, and SEQ ID NO:3 joined contiguously as depicted in FIG. 1.

2. A cloning vector comprising the nucleic acid sequence of claim 1.

3. A host cell comprising the vector of claim 2.

4. An isolated nucleic acid fragment deposited with the American Type Culture Collection under Accession No. 75334 having the sequence of SEQ ID NO:1, SEQ ID NO:2, and SEQ ID NO:3.

5. A diagnostic nucleic acid sequence that is associated with pyrethroid sensitivity and resistance traits, wherein said sequence consists of nucleotides 48–567 of SEQ ID NO:2 joined contiguously to nucleotides 1–568 of SEQ ID NO:3, corresponding to nucleotides 4116 to 4399 of the Heliothis sequence depicted in FIG. 1.

6. A cloning vector comprising the nucleic acid sequence of claim 5.

7. A host cell comprising a vector as defined in claim 6.

8. A nucleic acid probe for detecting an RFLP in a non-dipteran insect, wherein said RFLP is characteristic of pyrethroid-sensitive and pyrethroid-resistant individuals, said probe having a nucleic acid sequence that is associated with said pyrethroid sensitivity and pyrethroid resistance, and having a nucleic acid sequence consisting of nucleotides 48–567 of SEQ ID NO:2 joined contiguously to nucleotides 1–568 of of SEQ ID NO:3, corresponding to nucleotides 4116 to 4399 of the Heliothis sequence of FIG. 1.

9. An isolated nucleic acid consisting of nucleotides 48–568 of SEQ ID NO:2 joined contiguously to nucleotides 1–568 of SEQ ID NO:3, corresponding to nucleotides 4116 to 4399 of the Heliothis sequence of FIG. 1.

10. A method for identifying a nucleic acid encoding a sodium channel of an insect by a step of screening a genomic or a cDNA library from said insect with a nucleic acid probe comprising nucleotides 48–567 of SEQ ID NO:2 joined contiguously to nucleotides 1–568 of SEQ ID NO:3, corresponding to nucleotides 4116–4399 of the Heliothis sequence of FIG. 1.

11. The method of claim 10, further comprising the step of isolating the nucleic acid encoding said sodium channel identified in said screening step.

12. The method of claim 10, wherein said insect is a non-dipteran insect.

13. The method of claim 12, wherein said non-dipteran insect is selected from the group consisting of lepidopteran, coleopteran and homopteran.

14. The method of claim 10, wherein said insect is a lepidopteran.

15. The method of claim 14, wherein said lepidopteran is selected form the group consisting of *Heliothis virescens, Heliothis armigera, Helicoverpa zea, Spodoptera literalis,* and *Spodoptera exiuga.*

* * * * *

SEQUENCE LISTING (1) GENERAL INFORMATION:

(iii) NUMBER OF SEQUENCES: 40

(2) INFORMATION FOR SEQ ID NO:1:

(i) SEQUENCE CHARACTERISTICS:
        (A) LENGTH: 2416 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

```
AATTCACTAT ACCAGGTAAC TTTTTGATAC CTAGTTTAAA ATAAGATACT GTTGTTATCT      60

AATAGGATTT TAAGAGTTGT CATAAACGTA ATGTTAATTT TTCAGGCGAC AATAAATACA     120

AGAAAGGGCA AAATTTTGTT AAATAATATT AACGCAWTAA CAGATAATCA TAGAGACAAC     180

CGTTTAGACT GTGAATTAAA TCATCACGGG TATCCTATAC AGGTAAATAT TTGTCGTCAC     240

AGCTTKCTAA TAAATCACAA TCAAGTTTCT GTACTAAGAA CACAATTTCT CGTTTAGGAT     300

GACGATACAA TTAGTCAAAA ATCGTACGGC AGTCATAAAA TCAGGTCGTT CAAAGATGAA     360

AGTCATAAAG GTTCCGCAGA CACGATAGAT GGCGAMGMGM MGAAGGACGC TAGTAAAGAG     420

GAATTGGGTT TAGAAGAAGG TCAGTGTAAA ACTGCAATTN AAAATTAACA GAATTGAACT     480

AAGCCATATT TGGACAATTT GCATATAATT AATGTGTTAC AGAAATGGTT GAAGAAGAGG     540

AAGATGGGAA GTTAGACGGA GGTCTAGGCA AAACAGACAT TATAGTGGCC GCAGATGAAG     600

AAGTTGTTGA CGATAGCCCT GCTGACTGCT GTCCAGAGCC ATGTTACGCG AAGTTTCCAT     660

TCCTTGTGGG TGATGATGAA TCTCCCTTTT GGCAAGGCTG GGGCATGCTT CGGTTGAAAA     720

CCTTCAAACT CATTGAGAAC ACATATTTCG AAACGGCTGT GATTACAATG ATTTTGCTCA     780

GTAGTTTGGC TTTGGTAAGT TCTCAAATAA TTTTCTGAAC ACTTTGTTTC ACATAGTAAG     840

GGAGCAAATT ATGTTCATGA CGAAACTTYK CTGTCTTTAC AGGCTTTAGA AGATGTAAAT     900

TTACCACATC GACCGATTCT TCAAGATATC TTGTATTATA TGGATCGGAT CTTCACCGTC     960

ATTTTCTTCA TCGAGATGTT GATCAAATGG CTTGCCCTTG GCTTCCAGAA ATACTTCACA    1020

AATGCGTGGT GCTGGCTCGA CTTCATCATT GTCATGGTAA TATTACTATA AATATATTTG    1080

CTTTCGTATC ATTTGAACTA ACAGTTTCCT TGCAGATTAG ATTGGTAAAA CGTAGATTAT    1140
```

```
GATTATGGAA TTTGAACTTG TAAGTTCTGT ATAATGTGAA AGACAAAATT AAGGTTCAGG    1200

TCGGTCTTTG AAGTTTATCC TGCCGCCTCT CAGCGAGGTA AAGCTGGGAA GAATAATTTA    1260

TACAGTGTTA AGTATACCTA GATGTAAGGA ATATATTGTA TACTAAAGTA AATGACGATT    1320

GGTGTGGCGT TAGTTGTCGC TCGTAAACCA CGGNGCAGTG ATGSTGGCGS GACGACATCC    1380

CNGTTCCGCT CGATGCACGT TGNGNGCGCT GCGGCTCCGC GCGGTCTCTC GCTGGGAGGG    1440

CATGCGCGTG AGTAGGACGG CACACCACTC GTGCGCAGGC TGTGTTGGTA TCGTTGCGCT    1500

GCACATCCAC ACGATTGTTT CACTCTACTT TCTGCTGAGA AATCAGTGCA ACATGGTGTT    1560

GCTAATCGAA ATAAGCAACC AAACCTTCCG ACAGAGATTT TTATCTCGAA CCACTTTGTG    1620

AAATGTGAAC TCTGATTCAT ATTCAACTAA TCTCTTAATA AAGTTTGTTG TAAATATTTT    1680

CTAATTCTAC TGTGTTTGAC GTGCAGCGCA ACTCAAAGCG TGCAGCTTTG ATTGTTCGAT    1740

GTCTATGGCA GTGGAAACTC CGAACGGCCT CACCTCGCTG CCTCGAGCTC TCGATGTCGT    1800

ATTGTTTGTT TATGGAAACC GCTTCATGTG ACTCTATAAC CCACGACCCC CGCTATATGA    1860

ATACCTGTGR CCGTATATAT AAAAACCTCC ACAGAGTGAC TTGAAATCCT TATACTTTCA    1920

AGTGCATGAA ACAACACGTC TTCTATCTTT GTGCTGTTGT GCGAGATAGT GCGTTTTCAC    1980

GTACTACTCA CATTACCCAC ATCTGTCGGG GATAAAATCC GASATTTGAA AGAAAAGCTT    2040

TAAAACTGAA AATGGCACGT GATGTTGGTT GCTGTCGATG TCATTACAAA GCAAACTATA    2100

AATACCTATA CTATATACAT ATCTTTGATA TTTGTTCTTA ATATGATGTG ATGTAGCTTT    2160

ATTTTAGGGA CATCAGAGAA ACGGTAGCCT AAGCTCAAAA TTAGAGCTTT TTGTAAAATC    2220

AATCCTGTTA ATTGCTATAT AATTATTTCC ATTTCTTTTA TTCTCTGATG KYCYYMAARK    2280

WAMYTCGATG TAACCTTATG TGTAACTTGA GTGAATATCA CGTTCCTATC CCTCTGATTA    2340

TGCTGCAATA GGAACTTCTG TTTCCAAATG AATCTTGAGA TTTTCTTCTT TATAGTATCA    2400

TATCCTTAGG TTTGTA                                                    2416

(2) INFORMATION FOR SEQ ID NO:2:

(i) SEQUENCE CHARACTERISTICS:
            (A) LENGTH: 567 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:2:

ATTAGCGTTC AAAAGCGATG CGAAGCTGGG ACTGCGCTCT CAGGCCATGA GCCGCATGCA      60

GGGCATGAGG GTACGTACCA CCCTGTGCTG CCGACAACAC CCTATCGCTC ATCCATCCAC     120

CACACACTTC GCTCCACACT TCACATTCAC ATTTCTATTT CAACTTCTAC GATCATTTTT     180

TAACATTTTA AAATTTCCAA CGTRCCAGCC GTACTMGGGC TCCTTTTTTC GATATTTCTG     240

CATSAATCAC CGGATCAAAA TTTGTTTTTA ATAGTTAATT TGGACAGTTA TCCGATTCAT     300

TGGCAGTAGT CGATTGAAGT AATTATTAGT GAATCATTTT GAAGTGGTCG GTGGCACCCC     360

TGAATGGCTT AGTATCATCA CTGTTCGTCA TAAACCTCTT TTAGAAAGGG TCAATGGGAT     420

TTATTGTGGA GAGATATTYR TCCATGTTTT GGTCTCTTTT CTATTGGTCT TATTATTAGC     480

TAGATTAGAC TTTTGTAATT ACTTAGTTAT TTGGAATGCT AATTTATATT CTGCACCTTA     540

GATTTTTTCT TCTTGTATCT TCATCGA                                        567

(2) INFORMATION FOR SEQ ID NO:3:
```

(i) SEQUENCE CHARACTERISTICS:
    (A) LENGTH: 2279 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:3:

| | | | | | |
|---|---|---|---|---|---|
| GCTAACTGCT | ACATAGTTAC | TGCACAGTAT | TAATGACATT | AACGTCCTTA | TATCCCAACT | 60
| AATAATGCGC | CCACTAACAA | ATGCACGCCA | TTGATATAAG | AAAGGAGACG | TATCAGTACT | 120
| TCCAATATAT | CCTTCGTGAC | CAGTGTAGTA | ATACGTACGT | ATGTGACAGG | TGGTGGTAAA | 180
| CGCTCTCGTG | CAAGCGATCC | CGTCCATCTT | CAACGTGTTG | TTGGTGTGTC | TTATCTTCTG | 240
| GCTGATCTTC | GCCATCATGG | GAGTACAACT | GTTCGCTGGC | AAATATTTCA | AGGTATTAAT | 300
| TTATTAACAT | AACAAAAAAA | TATTTCAATT | CGTAAAATCT | TATTAGTGTG | TTCAAAATTT | 360
| CTAACATGTT | TTTCTTTGTT | CTGTTCTAGT | GCGTCGACCT | CAACCACACG | ACGTTGAGCC | 420
| ACGAAATCAT | CCCAGACCGG | AATGCGTGCA | TCTTAGAGAA | CTACACCTGG | GAGAACTCAC | 480
| CGATGAACTT | TGACCATGTC | GGCAAGGCGT | ATCTCTGCCT | GTTCCAAGTG | GCCACCTTCA | 540
| AGGGATGGAT | ACAGATCATG | AACGACGCTA | TTGATTCGAG | AGAAGTATGG | CTACTATTTC | 600
| TTTTCCTTTT | GTTCATAAGT | TCATAAATTA | ATATCAATAA | AAATATCACG | CAATACAATA | 660
| AATGATATTG | TTAATGCCAG | GTGGGCCGGC | AACCTATACG | CGAGACGAAC | ATCTACATGT | 720
| ACCTGTACTT | CGTGTTCTTC | ATCATATTTG | GCTCATTCTT | CACTCTCAAC | CTATTCATCG | 780
| GTGTGATCAT | CGACAACTTT | AACGAACAGA | AGAAGAAAGC | CGGCGGCAGC | CTTGAGATGT | 840
| TCATGACTGA | GGACCAGAAG | AAATACTACA | ATGCCATGAA | GAAAATGGGT | TCTAAAAAAC | 900
| CTTTAAAAGC | TATCCCGAGA | CCGAAGGTAA | CAGACGATTG | CATTGTTTTT | TGACCTCAAT | 960
| GGAAACATAT | CCAAGGAGGA | GCGAGTCTTA | TATTTGAAAC | TTGATAGTAA | TATTGTTGTA | 1020
| TATTTTATAA | TTTCATAAAC | AGCAGTACTG | CGGTAAACCA | TTGTTTTCAA | CGCCAGAAAC | 1080
| TGCAGGACGT | TTAATTATTG | AGGGATGATT | TTGCCTAGAA | TCTATTCTAA | GATTGATTTG | 1140
| GAGCCGTCCA | CTTCCCAACG | ACAGTTGCAG | CATCTATGCC | ACCGGACCAC | GTCGTTGTAC | 1200
| CCAGATAAGA | AAGCTTTCTA | CCTAAATAAA | CACTAACTGA | AACTGTTTGT | TCCAGTGGCG | 1260
| GCCACAAGCG | ATCGTGTTCG | AGATAGTGAC | GGACAAGAAG | TTCGACATGA | TCATCATGTT | 1320
| GTTCATCGGC | CTCAACATGT | TGACGATGAC | GCTCGATCAC | TACCAGCAGT | CGGAGACCTT | 1380
| CAGCACTGTC | CTCGACTACC | TCAACATGAT | ATTCATCGTG | ATATTCAGTT | CAGAGTGCCT | 1440
| ATTAAAAATG | TTCGCCTTAC | GCTACCATTA | CTTTGTTGAG | CCATGGAACT | TGTTCGATTT | 1500
| CGTAGTAGTC | AATTTCTCAA | TTCTTAGTGA | GTATTTTGGG | TCTCCTGTTA | TTCCAATAGT | 1560
| AAAGTGTTTT | CCATTTATAA | TTTACTAATG | ATACACTCTC | TTTGTTCTCA | GGTTTGGTAT | 1620
| TGAGTGATAT | TATAGAAAAA | TATTTTGTGT | CACCCACGTT | ACTGAGGGTG | GTGAGAGTAG | 1680
| CGAAGGTCGG | TCGTGTGTTG | CGTCTCGTGA | AGGGTGCGAA | GGGTATCCGG | ACGTTATTGT | 1740
| TCGGGCTGGC | CATGTCACTG | CCAGCCTTAT | TCAACATCTG | TCTGCTGCTG | TTCCTTGTGA | 1800
| TGTTCATCTT | CGCCATCTTC | GGCATGTCGT | TCTTTATGCA | CGTCAAAGAC | AAAGGTGGTC | 1860
| TCGACGACGT | GTACAACTTC | AAGACCTTCG | TGCAGAGTAT | GATCCTGCTA | TTTCAGGTCA | 1920
| GTGTTACTAA | TCATACTTTA | GCGCCTCCTG | GTTGCTTGAG | GATGAATGAC | CACAAGCAAC | 1980
| CAGCAGGGTT | TATTCGTTCA | AATTGAAAGT | TAATTTTTAG | CCGTTCAAGC | ATCTAGTGTA | 2040

```
TGCTAATCTG TCTTATCGTT TGTCAGATGT CGACGTCNGC CGGCTGGGAC GGCGTGCTGG    2100

ACGGCATCAT CAACGAGGAG GAGTGCGANC TGCCGGACAA CGAGCGCGGC TACCCCGGCA    2160

ACTGCGGCTC TGCNACCATC GGCATCACCT ACCTGCTGTC CTACCTCGTC ATCTCCTTCC    2220

TCATCGTCAT CAACATGTAC ATCGCCGTCA TTCTCGAGAA TTACTCGCAG GCAAGTTGA    2279
```

(2) INFORMATION FOR SEQ ID NO:4:

(i) SEQUENCE CHARACTERISTICS:
        (A) LENGTH: 196 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Asp Asp Asp Thr Ile Ser Gln Lys Ser Tyr Gly Ser His Lys Ile Arg
1               5                  10                  15

Ser Phe Lys Asp Glu Ser His Lys Gly Ser Ala Asp Thr Ile Asp Gly
            20                  25                  30

Xaa Xaa Xaa Lys Asp Ala Ser Lys Glu Glu Leu Gly Leu Glu Glu Glu
        35                  40                  45

Met Val Glu Glu Glu Asp Gly Lys Leu Asp Gly Gly Leu Gly Lys
    50                  55                  60

Thr Asp Ile Ile Val Ala Ala Asp Glu Glu Val Val Asp Asp Ser Pro
65                  70                  75                  80

Ala Asp Cys Cys Pro Glu Pro Cys Tyr Ala Lys Phe Pro Phe Leu Val
                85                  90                  95

Gly Asp Asp Glu Ser Pro Phe Trp Gln Gly Trp Gly Met Leu Arg Leu
                100                 105                 110

Lys Thr Phe Lys Leu Ile Glu Asn Thr Tyr Phe Glu Thr Ala Val Ile
            115                 120                 125

Thr Met Ile Leu Leu Ser Ser Leu Ala Leu Ala Leu Glu Asp Val Asn
130                 135                 140

Leu Pro His Arg Pro Ile Leu Gln Asp Ile Leu Tyr Tyr Met Asp Arg
145                 150                 155                 160

Ile Phe Thr Val Ile Phe Phe Ile Glu Met Leu Ile Lys Trp Leu Ala
                165                 170                 175

Leu Gly Phe Gln Lys Tyr Phe Thr Asn Ala Trp Cys Trp Leu Asp Phe
                180                 185                 190

Ile Ile Val Met
        195
```

(2) INFORMATION FOR SEQ ID NO:5:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Ala Met Ser Arg Met Gln Gly Met Arg
1               5
```

(2) INFORMATION FOR SEQ ID NO:6:

(i) SEQUENCE CHARACTERISTICS:
    (A) LENGTH: 452 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:6:

```
Val Val Val Asn Ala Leu Val Gln Ala Ile Pro Ser Ile Phe Asn Val
 1               5                  10                  15

Leu Leu Val Cys Leu Ile Phe Trp Leu Ile Phe Ala Ile Met Gly Val
             20                  25                  30

Gln Leu Phe Ala Gly Lys Tyr Phe Lys Cys Val Asp Leu Asn His Thr
         35                  40                  45

Thr Leu Ser His Glu Ile Ile Pro Asp Arg Asn Ala Cys Ile Leu Glu
     50                  55                  60

Asn Tyr Thr Trp Glu Asn Ser Pro Met Asn Phe Asp His Val Gly Lys
65                  70                  75                  80

Ala Tyr Leu Cys Leu Phe Gln Val Ala Thr Phe Lys Gly Trp Ile Gln
                 85                  90                  95

Ile Met Asn Asp Ala Ile Asp Ser Arg Glu Val Gly Arg Gln Pro Ile
            100                 105                 110

Arg Glu Thr Asn Ile Tyr Met Tyr Leu Tyr Phe Val Phe Phe Ile Ile
        115                 120                 125

Phe Gly Ser Phe Phe Thr Leu Asn Leu Phe Ile Gly Val Ile Ile Asp
    130                 135                 140

Asn Phe Asn Glu Gln Lys Lys Lys Ala Ala Gly Ser Leu Glu Met Phe
145                 150                 155                 160

Met Thr Glu Asp Gln Lys Lys Tyr Tyr Asn Ala Met Lys Lys Met Gly
                165                 170                 175

Ser Lys Lys Pro Leu Lys Ala Ile Pro Arg Pro Lys Trp Arg Pro Gln
            180                 185                 190

Ala Ile Val Phe Glu Ile Val Thr Asp Lys Lys Phe Asp Met Ile Ile
        195                 200                 205

Met Leu Phe Ile Gly Leu Asn Met Leu Thr Met Thr Leu Asp His Tyr
    210                 215                 220

Gln Gln Ser Glu Thr Phe Ser Thr Val Leu Asp Tyr Leu Asn Met Ile
225                 230                 235                 240

Phe Ile Val Ile Phe Ser Ser Glu Cys Leu Leu Lys Met Phe Ala Leu
                245                 250                 255

Arg Tyr His Tyr Phe Val Glu Pro Trp Asn Leu Phe Asp Phe Val Val
            260                 265                 270

Val Asn Phe Ser Ile Leu Ser Leu Val Leu Ser Asp Ile Ile Glu Lys
        275                 280                 285

Tyr Phe Val Ser Pro Thr Leu Leu Arg Val Val Arg Val Ala Lys Val
    290                 295                 300

Gly Arg Val Leu Arg Leu Val Lys Gly Ala Lys Gly Ile Arg Thr Leu
305                 310                 315                 320

Leu Phe Gly Leu Ala Met Ser Leu Pro Ala Leu Phe Asn Ile Cys Leu
                325                 330                 335

Leu Leu Phe Leu Val Met Phe Ile Phe Ala Ile Phe Gly Met Ser Phe
            340                 345                 350

Phe Met His Val Lys Asp Lys Gly Gly Leu Asp Asp Val Tyr Asn Phe
        355                 360                 365
```

```
Lys Thr Phe Val Gln Ser Met Ile Leu Leu Phe Gln Met Ser Thr Ser
    370                 375                 380

Ala Gly Trp Asp Gly Val Leu Asp Gly Ile Ile Asn Glu Glu Glu Cys
385                 390                 395                 400

Asp Leu Pro Asp Asn Glu Arg Gly Tyr Pro Gly Asn Cys Gly Ser Ala
                405                 410                 415

Thr Ile Gly Ile Thr Tyr Leu Leu Ser Tyr Leu Ala Ala Val Ile Ser
            420                 425                 430

Phe Leu Ile Val Ile Asn Met Tyr Ile Ala Val Ile Leu Glu Asn Tyr
            435                 440                 445

Ser Gln Ala Ser
    450

(2) INFORMATION FOR SEQ ID NO:7:

(i) SEQUENCE CHARACTERISTICS:
        (A) LENGTH: 5461 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

ATGACAGAAG ATTCCGACTC GATATCTGAG GAAGAACGCA GTTTGTTCCG TCCCTTTACC        60

CGCGAATCAT TGGTGCAAAT CGAACAACGC ATTGCCGCTG AACATGAAAA GCAGAAGGAG      120

CTGGAAAGAA AGAGAGCCGA GGGAGAGGTG CCGCGATATG GTCGCAAGAA AAACAAAAA       180

GAAATCCGAT ATGATGACGA GGACGAGGAT GAAGGTCCAC AACCGGATCC TACACTTGAA      240

CAGGGTGTGC CAATACCTGT TCGATTGCAG GGCAGCTTCC CGCCGGAATT GGCCTCCACT      300

CCTCTCGAGG ATATCGATCC CTACTACAGC AATGTACTGA CATTCGTAGT TGTAAGCAAA      360

GGAAAAGATA TTTTTCGCTT TTCTGCATCA AAAGCAATGT GGATGCTCGA TCCATTCAAT      420

CCGATACGTC GTGTGGCCAT TTACATTCTA GTGCATCCAT TATTTTCCCT ATTCATCATC      480

ACCACAATTC TCGTCAACTG CATCCTGATG ATAATGCCGA CAACGCCCAC GGTTGAGTCC      540

ACTGAGGTGA TATTCACCGG AATCTACACA TTTGAATCAG CTGTTAAAGT GATGGCACGA      600

GGTTTCATTT TATGCCCGTT TACGTATCTT AGAGATGCAT GGAATTGGCT GGACTTCGTA      660

GTAATAGCTT TAGCTTATGT GACCATGGGT ATAGATTTAG GTAATCTAGC AGCCCTGCGA      720

ACGTTTAGGG TGCTGCGAGC GCTTAAAACC GTAGCCATTG TGCCAGGCTT GAAGACCATC      780

GTCGGCGCCG TCATCGAATC GGTGAAGAAT CTGCGCGATG TGATTATCCT GACCATGTTC      840

TCCCTGTCGG TGTTCGCGTT GATGGGCCTA CAGATCTATA TGGGCGTGCT CACCGAGAAG      900

TGCATCAAGA AGTTCCCGCT GGACGGTTCC TGGGGCAATC TGACCGACGA GAACTGGGAC      960

TATCACAATC GCAATAGCTC CAATTGGTAT TCCGAGGACG AGGGCATCTC ATTTCCGTTA     1020

TGCGGCAATA TATCCGGTGC GGGGCAATGC GACGACGATT ACGTGTGCCT GCAGGGGTTT     1080

GGTCCGAATC CGAATTATGG CTACACCAGC TTCGATTCGT TCGGATGGGC TTTCCTGTCC     1140

GCCTTCCGGC TGATGACACA GGACTTCTGG GAGGATCTGT ACCAGCTGGT GTTGCGCGCC     1200

GCCGGACCAT GGCACATGCT GTTCTTTATA GTCATCATCT TCCTAGGTTC ATTCTATCTT     1260

GTGAATTTGA TTTTGGCCAT TGTTGCCATG TCGTATGACG AATTGCAAAG GAAGGCCGAA     1320

GAAGAAGAGG CTGCCGAAGA GGAGGCGATA CGTGAAGCGG AAGAAGCTGC CGCCGCCAAA     1380

GCGGCCAAGC TGGAGGAGCG GGCCAATGCG CAGGCTCAGG CAGCAGCGGA TGCGGCTGCC     1440
```

```
-continued

GCCGAAGAGG CTGCACTGCA TCCGGAAATG GCCAAGAGTC CGACGTATTC TTGCATCAGC   1500

TATGAGCTAT TTGTTGGCGG CGAGAAGGGC AACGATGACA ACAACAAAGA GAAGATGTCC   1560

ATTCGGAGCG TCGAGGTGGA GTCGGAGTCG GTGAGCGTTA TACAAAGACA CCAGCACCCT   1620

ACCACAGCAC ACCAAGCTAC CAAAGTTCGT AAAGTGAGCA CGTACACGAT ACGGAACGGA   1680

CGTGGCCGCT TTGGTATACC CGGTAGCGAT CGTAAGCCAT TGGTATTGTC AACATATCAG   1740

GATGCCCAGC AGCACTTGCC CTATGCCGAC GACTCGAATG CCGTCACCCC GATGTCCGAA   1800

GAGAATGGGG CCATCATAGT GCCCGTGTAC TATGGCAATC TAGGCTCCCG ACACTCATCG   1860

TATACCTCGC ATCAGTCCCG AATATCGTAT ACCTCACATG GCGATCTACT CGGCGGCATG   1920

GCCGTCATGG GCGTCAGCAC AATGACCAAG GAGAGCAAAT TGCGCAACCG CAACACACGC   1980

AATCAATCAG TGGGCGCCAC CAATGGCGGC ACCACCTGTC TGGACACCAA TCACAAGCTC   2040

GATCATCGCG ACTACGAAAT TGGCCTGGAG TGCACGGACG AAGCTGGCAA GATTAAACAT   2100

CATGACAATC CTTTTATCGA GCCCGTCCAG ACACAAACGG TGGTTGATAT GAAAGATGTG   2160

ATGGTCCTGA ATGACATCAT CGAACAGGCC GCTGGTCGGC ACAGTCGGGC AAGCGATCGC   2220

GGTGTCTCCG TTTACTATTT CCCAACAGAG GACGATGACG AGGATGGGCC GACGTTCAAA   2280

GACAAGGCAC TCGAAGTGAT CCTCAAAGGC ATCGATGTGT TTTGTGTGTG GGACTGTTGC   2340

TGGGTTTGGT TGAAATTTCA GGAGTGGGTA TCGCTCATCG TCTTCGATCC CTTCGTCGAG   2400

CTCTTCATCA CGCTGTGCAT TGTGGTCAAC ACGATGTTCA TGGCAATGGA TCACCACGAT   2460

ATGAACAAGG AGATGGAACG CGTGCTCAAG AGTGGCAACT ATTTCTTCAC CGCCACCTTT   2520

GCCATCGAGG CCACCATGAA GCTAATGGCC ATGAGCCCCA AGTACTATTT CCAGGAGGGC   2580

TGGAACATCT TCGACTTCAT TATCGTGGCC CTATCGCTAT TGAACTGGG ACTCGAGGGT   2640

GTCCAGGGTC TGTCCGTATT GCGTTCCTTT CGATTGCTGC GTGTATTCAA ACTGGCCAAG   2700

TCTTGGCCCA CACTTAATTT ACTCATTTCG ATTATGGGAC GCACCATGGG CGCTTTGGGT   2760

AATCTGACAT TTGTACTTTG CATTATCATC TTCATCTTTG CGGTGATGGG AATGCAACTG   2820

TTCGGAAAGA ATTATCATGA TCACAAGGAC CGCTTTCCGG ATGGCGACCT GCCGCGCTGG   2880

AACTTCACCG ACTTTATGCA CAGCTTCATG ATCGTGTTCC GGGTGCTCTG CGGAGAATGG   2940

ATCGAGTCCA TGTGGGACTG CATGTACGTG GGCGATGTCT CGTGCATTCC CTTCTTCTTG   3000

GCCACCGTTG TCATCGGCAA TCTTGTGGTA CTTAACCTTT TCTTAGCCTT GCTTTTGTCC   3060

AATTTTGGCT CATCTAGCTT ATCAGCGCCG ACTGCCGATA ACGATACGAA TAAAATAGCC   3120

GAGGCCTTCA ATCGAATTGG CCGATTTAAA AGTTGGGTTA AGCGTAATAT TGCTGATTGT   3180

TTCAAGTTAA TACGTAACAA ATTGACAAAT CAAATAAGTG ATCAACCATC AGAGCATGGT   3240

GACAACGAAC TGGAGCTGGG CCACGACGAG ATCCTCGCCG ACGGCCTCAT CAAGAAGGGG   3300

ATCAAGGAGC AGACGCAACT GGAGGTGGCC ATCGGGGATG GCATGGAATT CACGATACAC   3360

GGCGACATGA AGAACAACAA GCCGAAGAAA TCCAAATATC TAAATAACGC AACGGACGAC   3420

GACACTGCCA GCATTAACTC ATATGGTAGC CATAAGAATC GACCATTCAA GGACGAGAGC   3480

CACAAGGGCA GCGCCGAGAC GATGGAGGGC GAGGAGAAGC GCGACGCCAG CAAGGAGGAT   3540

TTAGGTCTCG ACGAGGAACT GGACGAGGAG GGCGAATGCG AGGAGGGCCC GCTCGACGGT   3600

GATATCATTA TTCATGCACA CGACGAGGAT ATACTCGATG AATATCCAGC TGATTGCTGC   3660

CCCGATTCGT ACTATAAGAA ATTTCCGATC TTAGCCGGTG ACGATGACTC GCCGTTCTGG   3720

CAAGGATGGG GCAATTTACG ACTGAAAACT TTTCGATTAA TTGAGGATAA ATATTTTGAA   3780

ACAGCTGTTA TCACTATGAT TTTAATGAGT AGCTTAGCTT TGGCATTAGA AGATGTACAT   3840
```

-continued

```
CTGCCACAAA GACCCATACT GCAGGATATT TTATACTATA TGGACAGAAT ATTTACGGTT    3900

ATATTCTTCT TGGAAATGTT AATCAAGTGG TTGGCGCTCG GCTTCAAAGT GTACTTGACC    3960

AACGCGTGGT GTTGGCTCGA TTTCGTGATT GTCATGGTAT CGCTTATCAA CTTCGTTGCT    4020

TCACTTGTTG GAGCTGGTGG TATTCAAGCC TTCAAGACTA TGCGAACGTT AAGAGCACTG    4080

AGACCACTAC GTGCCATGTC CCGTATGCAG GGCATGAGGG TCGTCGTTAA TGCGCTGGTA    4140

CAAGCTATAC CGTCCATCTT CAATGTGCTA TTGGTGTGTC TAATATTTTG GCTAATTTTT    4200

GCCATAATGG GTGTACAGCT TTTTGCTGGA AAATATTTTA AGTGCGAGGA CATGAATGGC    4260

ACGAAGCTCA GCCACGAGAT CATACCAAAT CGCAATGCCT GCGAGAGCGA GAACTACACG    4320

TGGGTGAATT CAGCAATGAA TTTCGATCAT GTAGGTAACG CGTATCTGTG CCTTTTCCAA    4380

GTGGCCACCT TCAAAGGCTG GATACAAATC ATGAACGATG CTATCGATTC ACGAGAGGTG    4440

GACAAGCAAC CAATTCGTGA AACGAACATC TACATGTATT TATATTTCGT ATTCTTCATC    4500

ATATTTGGAT CATTTTTCAC ACTCAATCTG TTCATTGGTG TTATCATTGA TAATTTTAAT    4560

GAGCAAAAGA AAAAGCAGG TGGATCATTA GAAATGTTCA TGACAGAAGA TCAGAAAAAG    4620

TACTATAGTG CTATGAAAAA GATGGGCTCT AAAAAACCAT TAAAAGCCAT TCCAAGACCA    4680

AGGTGGCGAC CACAAGCAAT AGTCTTTGAA ATAGTAACCG ATAAGAAATT CGATATAATC    4740

ATTATGTTAT TCATTGGTCT GAACATGTTC ACCATGACCC TCGATCGTTA CGATGCGTCG    4800

GACACGTATA ACGCGGTCCT AGACTATCTC AATGCGATAT TCGTAGTTAT TTTCAGTTCC    4860

GAATGTCTAT TAAAAATATT CGCTTTACGA TATCACTATT TTATTGAGCC ATGGAATTTA    4920

TTTGATGTAG TAGTTGTCAT TTTATCCATC TTAGGTCTTG TACTTAGCGA TATTATCGAG    4980

AAGTACTTCG TGTCGCCGAC CCTGCTCCGA GTGGTGCGTG TGGCGAAAGT GGGCCGTGTC    5040

CTTCGACTGG TGAAGGGAGC CAAGGGCATT CGGACACTGC TCTTCGCGTT GGCCATGTCG    5100

CTGCCGGCCC TGTTCAACAT CTGCCTGCTG CTGTTCCTGG TCATGTTCAT CTTTGCCATT    5160

TTCGGCATGT CGTTCTTCAT GCACGTGAAG GAGAAGAGCG GCATTAACGA CGTCTACAAC    5220

TTCAAGACCT TTGGCCAGAG CATGATCCTG CTCTTTCAGA TGTCGACGTC AGCCGGTTGG    5280

GATGGTGTAC TGGACGCCAT TATCAATGAG GAAGCATGCG ATCCACCCGA CAACGACAAA    5340

GGCTATCCGG GCAATTGTGG TTCAGCGACC GTTGGAATAA CGTTTCTCCT CTCATACCTA    5400

GTTATAAGCT TTTTGATAGT TATTAATATG TACATTGCTG TCATTCTCGA GAACGGAATT    5460

C                                                                   5461
```

(2) INFORMATION FOR SEQ ID NO:8:

(i) SEQUENCE CHARACTERISTICS:
        (A) LENGTH: 1820 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Met Thr Glu Asp Ser Asp Ser Ile Ser Glu Glu Arg Ser Leu Phe
1               5                  10                  15

Arg Pro Phe Thr Arg Glu Ser Leu Val Gln Ile Glu Gln Arg Ile Ala
                20                  25                  30

Ala Glu His Glu Lys Gln Lys Glu Leu Glu Arg Lys Arg Ala Glu Gly
            35                  40                  45
```

```
Glu Val Pro Arg Tyr Gly Arg Lys Lys Gln Lys Glu Ile Arg Tyr
 50                  55                  60

Asp Asp Glu Asp Glu Asp Gly Pro Gln Pro Asp Pro Thr Leu Glu
 65                  70                  75                  80

Gln Gly Val Pro Ile Pro Val Arg Leu Gln Gly Ser Phe Pro Glu
                 85                  90                  95

Leu Ala Ser Thr Pro Leu Glu Asp Ile Asp Pro Tyr Tyr Ser Asn Val
            100                 105                 110

Leu Thr Phe Val Val Ser Lys Gly Lys Asp Ile Phe Arg Phe Ser
            115                 120                 125

Ala Ser Lys Ala Met Trp Met Leu Asp Pro Phe Asn Pro Ile Arg Arg
130                 135                 140

Val Ala Ile Tyr Ile Leu Val His Pro Leu Phe Ser Leu Phe Ile Ile
145                 150                 155                 160

Thr Thr Ile Leu Val Asn Cys Ile Leu Met Ile Met Pro Thr Thr Pro
                165                 170                 175

Thr Val Glu Ser Thr Glu Val Ile Phe Thr Gly Ile Tyr Thr Phe Glu
            180                 185                 190

Ser Ala Val Lys Val Met Ala Arg Gly Phe Ile Leu Cys Pro Phe Thr
            195                 200                 205

Tyr Leu Arg Asp Ala Trp Asn Trp Leu Asp Phe Val Val Ile Ala Leu
210                 215                 220

Ala Tyr Val Thr Met Gly Ile Asp Leu Gly Asn Leu Ala Ala Leu Arg
225                 230                 235                 240

Thr Phe Arg Val Leu Arg Ala Leu Lys Thr Val Ala Ile Val Pro Gly
                245                 250                 255

Leu Lys Thr Ile Val Gly Ala Val Ile Glu Ser Val Lys Asn Leu Arg
            260                 265                 270

Asp Val Ile Ile Leu Thr Met Phe Ser Leu Ser Val Phe Ala Leu Met
            275                 280                 285

Gly Leu Gln Ile Tyr Met Gly Val Leu Thr Glu Lys Cys Ile Lys Lys
290                 295                 300

Phe Pro Leu Asp Gly Ser Trp Gly Asn Leu Thr Asp Glu Asn Trp Asp
305                 310                 315                 320

Tyr His Asn Arg Asn Ser Ser Asn Trp Tyr Ser Glu Asp Glu Gly Ile
                325                 330                 335

Ser Phe Pro Leu Cys Gly Asn Ile Ser Gly Ala Gly Gln Cys Asp Asp
            340                 345                 350

Asp Tyr Val Cys Leu Gln Gly Phe Gly Pro Asn Pro Asn Tyr Gly Tyr
            355                 360                 365

Thr Ser Phe Asp Ser Phe Gly Trp Ala Phe Leu Ser Ala Phe Arg Leu
370                 375                 380

Met Thr Gln Asp Phe Trp Glu Asp Leu Tyr Gln Leu Val Leu Arg Ala
385                 390                 395                 400

Ala Gly Pro Trp His Met Leu Phe Phe Ile Val Ile Ile Phe Leu Gly
                405                 410                 415

Ser Phe Tyr Leu Val Asn Leu Ile Leu Ala Ile Val Ala Met Ser Tyr
            420                 425                 430

Asp Glu Leu Gln Arg Lys Ala Glu Glu Glu Ala Glu Glu Glu
            435                 440                 445

Ala Ile Arg Glu Ala Glu Glu Ala Ala Ala Lys Ala Ala Lys Leu
450                 455                 460

Glu Glu Arg Ala Asn Ala Gln Ala Gln Ala Ala Ala Asp Ala Ala Ala
```

```
                465                 470                 475                 480
Ala Glu Glu Ala Ala Leu His Pro Glu Met Ala Lys Ser Pro Thr Tyr
                    485                 490                 495

Ser Cys Ile Ser Tyr Glu Leu Phe Val Gly Gly Glu Lys Gly Asn Asp
            500                 505                 510

Asp Asn Asn Lys Glu Lys Met Ser Ile Arg Ser Val Glu Val Glu Ser
        515                 520                 525

Glu Ser Val Ser Val Ile Gln Arg Gln Pro Ala Pro Thr Thr Ala His
    530                 535                 540

Gln Ala Thr Lys Val Arg Lys Val Ser Thr Tyr Thr Ile Arg Asn Gly
545                 550                 555                 560

Arg Gly Arg Phe Gly Ile Pro Gly Ser Asp Arg Lys Pro Leu Val Leu
                565                 570                 575

Ser Thr Tyr Gln Asp Ala Gln Gln His Leu Pro Tyr Ala Asp Asp Ser
            580                 585                 590

Asn Ala Val Thr Pro Met Ser Glu Glu Asn Gly Ala Ile Ile Val Pro
        595                 600                 605

Val Tyr Tyr Gly Asn Leu Gly Ser Arg His Ser Ser Tyr Thr Ser His
    610                 615                 620

Gln Ser Arg Ile Ser Tyr Thr Ser His Gly Asp Leu Leu Gly Gly Met
625                 630                 635                 640

Ala Val Met Gly Val Ser Thr Met Thr Lys Glu Ser Lys Leu Arg Asn
                645                 650                 655

Arg Asn Thr Arg Asn Gln Ser Val Gly Ala Thr Asn Gly Gly Thr Thr
            660                 665                 670

Cys Leu Asp Thr Asn His Lys Leu Asp His Arg Asp Tyr Glu Ile Gly
        675                 680                 685

Leu Glu Cys Thr Asp Glu Ala Gly Lys Ile Lys His His Asp Asn Pro
    690                 695                 700

Phe Ile Glu Pro Val Gln Thr Gln Thr Val Val Asp Met Lys Asp Val
705                 710                 715                 720

Met Val Leu Asn Asp Ile Ile Glu Gln Ala Ala Gly Arg His Ser Arg
                725                 730                 735

Ala Ser Asp Arg Gly Val Ser Val Tyr Tyr Phe Pro Thr Glu Asp Asp
            740                 745                 750

Asp Glu Asp Gly Pro Thr Phe Lys Asp Lys Ala Leu Glu Val Ile Leu
        755                 760                 765

Lys Gly Ile Asp Val Phe Cys Val Trp Asp Cys Cys Trp Val Trp Leu
    770                 775                 780

Lys Phe Gln Glu Trp Val Ser Leu Ile Val Phe Asp Pro Phe Val Glu
785                 790                 795                 800

Leu Phe Ile Thr Leu Cys Ile Val Val Asn Thr Met Phe Met Ala Met
                805                 810                 815

Asp His His Asp Met Asn Lys Glu Met Glu Arg Val Leu Lys Ser Gly
            820                 825                 830

Asn Tyr Phe Phe Thr Ala Thr Phe Ala Ile Glu Ala Thr Met Lys Leu
        835                 840                 845

Met Ala Met Ser Pro Lys Tyr Tyr Phe Gln Glu Gly Trp Asn Ile Phe
    850                 855                 860

Asp Phe Ile Ile Val Ala Leu Ser Leu Leu Glu Leu Gly Leu Glu Gly
865                 870                 875                 880

Val Gln Gly Leu Ser Val Leu Arg Ser Phe Arg Leu Leu Arg Val Phe
                885                 890                 895
```

-continued

```
Lys Leu Ala Lys Ser Trp Pro Thr Leu Asn Leu Leu Ile Ser Ile Met
            900                 905                 910
Gly Arg Thr Met Gly Ala Leu Gly Asn Leu Thr Phe Val Leu Cys Ile
            915                 920                 925
Ile Ile Phe Ile Phe Ala Val Met Gly Met Gln Leu Phe Gly Lys Asn
            930                 935             940
Tyr His Asp His Lys Asp Arg Phe Pro Asp Gly Asp Leu Pro Arg Trp
945                 950                 955                 960
Asn Phe Thr Asp Phe Met His Ser Phe Met Ile Val Phe Arg Val Leu
            965                 970                 975
Cys Gly Glu Trp Ile Glu Ser Met Trp Asp Cys Met Tyr Val Gly Asp
            980                 985                 990
Val Ser Cys Ile Pro Phe Phe Leu Ala Thr Val Val Ile Gly Asn Leu
            995                 1000                1005
Val Val Leu Asn Leu Phe Leu Ala Leu Leu Leu Ser Asn Phe Gly Ser
            1010                1015                1020
Ser Ser Leu Ser Ala Pro Thr Ala Asp Asn Asp Thr Asn Lys Ile Ala
1025                1030                1035                1040
Glu Ala Phe Asn Arg Ile Gly Arg Phe Lys Ser Trp Val Lys Arg Asn
            1045                1050                1055
Ile Ala Asp Cys Phe Lys Leu Ile Arg Asn Lys Leu Thr Asn Gln Ile
            1060                1065                1070
Ser Asp Gln Pro Ser Glu His Gly Asp Asn Glu Leu Glu Leu Gly His
            1075                1080                1085
Asp Glu Ile Leu Ala Asp Gly Leu Ile Lys Lys Gly Ile Lys Glu Gln
            1090                1095                1100
Thr Gln Leu Glu Val Ala Ile Gly Asp Gly Met Glu Phe Thr Ile His
1105                1110                1115                1120
Gly Asp Met Lys Asn Asn Lys Pro Lys Lys Ser Lys Tyr Leu Asn Asn
            1125                1130                1135
Ala Thr Asp Asp Asp Thr Ala Ser Ile Asn Ser Tyr Gly Ser His Lys
            1140                1145                1150
Asn Arg Pro Phe Lys Asp Glu Ser His Lys Gly Ser Ala Glu Thr Met
            1155                1160                1165
Glu Gly Glu Glu Lys Arg Asp Ala Ser Lys Glu Asp Leu Gly Leu Asp
1170                1175                1180
Glu Glu Leu Asp Glu Glu Gly Glu Cys Glu Glu Gly Pro Leu Asp Gly
1185                1190                1195                1200
Asp Ile Ile Ile His Ala His Asp Glu Asp Ile Leu Asp Glu Tyr Pro
            1205                1210                1215
Ala Asp Cys Cys Pro Asp Ser Tyr Tyr Lys Lys Phe Pro Ile Leu Ala
            1220                1225                1230
Gly Asp Asp Asp Ser Pro Phe Trp Gln Gly Trp Gly Asn Leu Arg Leu
            1235                1240                1245
Lys Thr Phe Arg Leu Ile Glu Asp Lys Tyr Phe Glu Thr Ala Val Ile
            1250                1255                1260
Thr Met Ile Leu Met Ser Ser Leu Ala Leu Ala Leu Glu Asp Val His
1265                1270                1275                1280
Leu Pro Gln Arg Pro Ile Leu Gln Asp Ile Leu Tyr Tyr Met Asp Arg
            1285                1290                1295
Ile Phe Thr Val Ile Phe Phe Leu Glu Met Leu Ile Lys Trp Leu Ala
            1300                1305                1310
```

-continued

```
Leu Gly Phe Lys Val Tyr Leu Thr Asn Ala Trp Cys Trp Leu Asp Phe
        1315                1320                1325

Val Ile Val Met Val Ser Leu Ile Asn Phe Val Ala Ser Leu Val Gly
            1330                1335                1340

Ala Gly Gly Ile Gln Ala Phe Lys Thr Met Arg Thr Leu Arg Ala Leu
1345                1350                1355                1360

Arg Pro Leu Arg Ala Met Ser Arg Met Gln Gly Met Arg Val Val Val
        1365                1370                1375

Asn Ala Leu Val Gln Ala Ile Pro Ser Ile Phe Asn Val Leu Leu Val
            1380                1385                1390

Cys Leu Ile Phe Trp Leu Ile Phe Ala Ile Met Gly Val Gln Leu Phe
        1395                1400                1405

Ala Gly Lys Tyr Phe Lys Cys Glu Asp Met Asn Gly Thr Lys Leu Ser
        1410                1415                1420

His Glu Ile Ile Pro Asn Arg Asn Ala Cys Glu Ser Glu Asn Tyr Thr
1425                1430                1435                1440

Trp Val Asn Ser Ala Met Asn Phe Asp His Val Gly Asn Ala Tyr Leu
            1445                1450                1455

Cys Leu Phe Gln Val Ala Thr Phe Lys Gly Trp Ile Gln Ile Met Asn
        1460                1465                1470

Asp Ala Ile Asp Ser Arg Glu Val Asp Lys Gln Pro Ile Arg Glu Thr
        1475                1480                1485

Asn Ile Tyr Met Tyr Leu Tyr Phe Val Phe Phe Ile Ile Phe Gly Ser
            1490                1495                1500

Phe Phe Thr Leu Asn Leu Phe Ile Gly Val Ile Ile Asp Asn Phe Asn
1505                1510                1515                1520

Glu Gln Lys Lys Lys Ala Gly Gly Ser Leu Glu Met Phe Met Thr Glu
            1525                1530                1535

Asp Gln Lys Lys Tyr Tyr Ser Ala Met Lys Lys Met Gly Ser Lys Lys
        1540                1545                1550

Pro Leu Lys Ala Ile Pro Arg Pro Arg Trp Arg Pro Gln Ala Ile Val
        1555                1560                1565

Phe Glu Ile Val Thr Asp Lys Lys Phe Asp Ile Ile Ile Met Leu Phe
        1570                1575                1580

Ile Gly Leu Asn Met Phe Thr Met Thr Leu Asp Arg Tyr Asp Ala Ser
1585                1590                1595                1600

Asp Thr Tyr Asn Ala Val Leu Asp Tyr Leu Asn Ala Ile Phe Val Val
            1605                1610                1615

Ile Phe Ser Ser Glu Cys Leu Leu Lys Ile Phe Ala Leu Arg Tyr His
        1620                1625                1630

Tyr Phe Ile Glu Pro Trp Asn Leu Phe Asp Val Val Val Val Ile Leu
        1635                1640                1645

Ser Ile Leu Gly Leu Val Leu Ser Asp Ile Ile Glu Lys Tyr Phe Val
        1650                1655                1660

Ser Pro Thr Leu Leu Arg Val Val Arg Val Ala Lys Val Gly Arg Val
1665                1670                1675                1680

Leu Arg Leu Val Lys Gly Ala Lys Gly Ile Arg Thr Leu Leu Phe Ala
            1685                1690                1695

Leu Ala Met Ser Leu Pro Ala Leu Phe Asn Ile Cys Leu Leu Leu Phe
        1700                1705                1710

Leu Val Met Phe Ile Phe Ala Ile Phe Gly Met Ser Phe Phe Met His
        1715                1720                1725

Val Lys Glu Lys Ser Gly Ile Asn Asp Val Tyr Asn Phe Lys Thr Phe
```

```
                1730              1735              1740
Gly Gln Ser Met Ile Leu Leu Phe Gln Met Ser Thr Ser Ala Gly Trp
1745              1750              1755              1760

Asp Gly Val Leu Asp Ala Ile Ile Asn Glu Glu Ala Cys Asp Pro Pro
            1765              1770              1775

Asp Asn Asp Lys Gly Tyr Pro Gly Asn Cys Gly Ser Ala Thr Val Gly
        1780              1785              1790

Ile Thr Phe Leu Leu Ser Tyr Leu Val Ile Ser Phe Leu Ile Val Ile
    1795              1800              1805

Asn Met Tyr Ile Ala Val Ile Leu Glu Asn Gly Ile
1810              1815              1820
```

(2) INFORMATION FOR SEQ ID NO:9:

(i) SEQUENCE CHARACTERISTICS:
        (A) LENGTH: 521 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
ATGAGCCGCA TGCAGGGCAT GAGGGTACGT ACCACCCTGT GCTGCCGACA CACCCTATC     60

GCTCATCCAT CCACCACACA CTTCGCTCCA CACTTCACAT TCACATTTCT ATTTCAACTT   120

CTACGATCAT TTTTTAACAT TTTAAAATTT CCAACGTRCC AGCCGTACTM GGGCTCCTTT   180

TTTCGATATT TCTGCATSAA TCACCGGATC AAAATTTGTT TTTAATAGTT AATTTGGACA   240

GTTATCCGAT TCATTGGCAG TAGTCGATTG AAGTAATTAT TAGTGAATCA TTTTGAAGTG   300

GTCGGTGGCA CCCCTGAATG GCTTAGTATC ATCACTGTTC GTCATAAACC TCTTTTAGAA   360

AGGGTCAATG GGATTTATTG TGGAGAGATA TTYRTCCATG TTTTGGTCTC TTTTCTATTG   420

GTCTTATTAT TAGCTAGATT AGACTTTTGT AATTACTTAG TTATTTGGAA TGCTAATTTA   480

TATTCTGCAC CTTAGATTTT TTCTTCTTGT ATCTTCATCG A                      521
```

(2) INFORMATION FOR SEQ ID NO:10:

(i) SEQUENCE CHARACTERISTICS:
        (A) LENGTH: 568 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
GCTAACTGCT ACATAGTTAC TGCACAGTAT TAATGACATT AACGTCCTTA TATCCCAACT    60

AATAATGCGC CCACTAACAA ATGCACGCCA TTGATATAAG AAAGGAGACG TATCAGTACT   120

TCCAATATAT CCTTCGTGAC CAGTGTAGTA ATACGTACGT ATGTGACAGG TGGTGGTAAA   180

CGCTCTCGTG CAAGCGATCC CGTCCATCTT CAACGTGTTG TTGGTGTGTC TTATCTTCTG   240

GCTGATCTTC GCCATCATGG GAGTACAACT GTTCGCTGGC AAATATTTCA AGGTATTAAT   300

TTATTAACAT AACAAAAAAA TATTTCAATT CGTAAAATCT TATTAGTGTG TTCAAAATTT   360

CTAACATGTT TTTCTTTGTT CTGTTCTAGT GCGTCGACCT CAACCACACG ACGTTGAGCC   420

ACGAAATCAT CCCAGACCGG AATGCGTGCA TCTTAGAGAA CTACACCTGG AGAAACTCAC   480

CGATGAACTT TGACCATGTC GGCAAGGCGT ATCTCTGCCT GTTCCAAGTG GCCACCTTCA   540
```

AGGGATGGAT ACAGATCATG AACGACGC                                                  568

(2) INFORMATION FOR SEQ ID NO:11:

(i) SEQUENCE CHARACTERISTICS:
           (A) LENGTH: 17 base pairs
           (B) TYPE: nucleic acid
           (C) STRANDEDNESS: single
           (D) TOPOLOGY: linear (ii) MOLECULE TYPE: DNA (genomic)

(iv) ANTI-SENSE: NO (vi) ORIGINAL SOURCE:
           (A) ORGANISM: Heliothis virescens (vii) IMMEDIATE SOURCE:
           (B) CLONE: SCp788+

(xi) SEQUENCE DESCRIPTION: SEQ ID NO:11:

AARACNATHG TNGGNCG                                                              17

(2) INFORMATION FOR SEQ ID NO:12:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (genomic)

(vi) ORIGINAL SOURCE:
           (A) ORGANISM: Heliothis virescens (vii) IMMEDIATE SOURCE:
           (B) CLONE: D&K+

(xi) SEQUENCE DESCRIPTION: SEQ ID NO:12:

AAYCCNAAYT AYGGNTAYAC                                                           20

(2) INFORMATION FOR SEQ ID NO:13:

(i) SEQUENCE CHARACTERISTICS:
           (A) LENGTH: 18 base pairs
           (B) TYPE: nucleic acid
           (C) STRANDEDNESS: single
           (D) TOPOLOGY: linear (ii) MOLECULE TYPE: DNA (genomic)

(vi) ORIGINAL SOURCE:
           (A) ORGANISM: Heliothis virescens (vii) IMMEDIATE SOURCE:
           (B) CLONE: SCp1153-

(xi) SEQUENCE DESCRIPTION: SEQ ID NO:13:

CCARAARTCY TGNGTCAT                                                             18

(2) INFORMATION FOR SEQ ID NO:14:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: DNA (genomic)

(vi) ORIGINAL SOURCE:

(A) ORGANISM: Heliothis virescens (vii) IMMEDIATE SOURCE:
         (B) CLONE: D&K-

(xi) SEQUENCE DESCRIPTION: SEQ ID NO:14:

YTCCCARAAR TCYTGNGTCA T                                        21

(2) INFORMATION FOR SEQ ID NO:15:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: Heliothis virescens (vii) IMMEDIATE SOURCE:
         (B) CLONE: HSC3455+

(xi) SEQUENCE DESCRIPTION: SEQ ID NO:15:

AAATCGTACG GCAGTCATAA                                          20

(2) INFORMATION FOR SEQ ID NO:16:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: Heliothis virescens (vii) IMMEDIATE SOURCE:
         (B) CLONE: HSCP3868-

(xi) SEQUENCE DESCRIPTION: SEQ ID NO:16:

ATGATGAAGT CGAGCCAGCA CC                                       22

(2) INFORMATION FOR SEQ ID NO:17:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: Heliothis virescens (vii) IMMEDIATE SOURCE:
         (B) CLONE: SCp3975+

(xi) SEQUENCE DESCRIPTION: SEQ ID NO:17:

ACNAAYGCNT GGTGYTGG                                            18

(2) INFORMATION FOR SEQ ID NO:18:

(i) SEQUENCE CHARACTERISTICS:
         (A) LENGTH: 20 base pairs
         (B) TYPE: nucleic acid
         (C) STRANDEDNESS: single

```
        (D) TOPOLOGY: linear (ii) MOLECULE TYPE: DNA (genomic)

(vi) ORIGINAL SOURCE:
         (A) ORGANISM: Heliothios virescens (vii) IMMEDIATE SOURCE:
          (B) CLONE: HSC4116+

(xi) SEQUENCE DESCRIPTION: SEQ ID NO:18:

TGAGCCGCAT GCAGGGCATG                                              20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Heliothis virescens (vii) IMMEDIATE SOURCE:
          (B) CLONE: HSC4105-

(xi) SEQUENCE DESCRIPTION: SEQ ID NO:19:

ACGTACCCTC ATGCCCTGCA                                              20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Heliothis virescens (vii) IMMEDIATE SOURCE:
          (B) CLONE: HSC4211+

(xi) SEQUENCE DESCRIPTION: SEQ ID NO:20:

CTGATCTTCG CCATCATGGG                                              20

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Heliothis virescens (vii) IMMEDIATE SOURCE:
          (B) CLONE: HSC4235+

(xi) SEQUENCE DESCRIPTION: SEQ ID NO:21:

ACAACTGTTC GCTGGMAAAT A                                            21

(2) INFORMATION FOR SEQ ID NO:22:
```

```
        (i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Heliothis virescens (vii) IMMEDIATE SOURCE:
            (B) CLONE: RRO8+

(xi) SEQUENCE DESCRIPTION: SEQ ID NO:22:

CAAATATTTC AAGGTATTAA T                                              21

(2) INFORMATION FOR SEQ ID NO:23:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Heliothis virescens (vii) IMMEDIATE SOURCE:
            (B) CLONE: SSO8+

(xi) SEQUENCE DESCRIPTION: SEQ ID NO:23:

AAAATATTTC AAGGTAAGCA G                                              21

(2) INFORMATION FOR SEQ ID NO:24:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Heliothis virescens (vii) IMMEDIATE SOURCE:
            (B) CLONE: HSC052-

(xi) SEQUENCE DESCRIPTION: SEQ ID NO:24:

ATTTTGAACA GACTAATAAG AT                                             22

(2) INFORMATION FOR SEQ ID NO:25:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Heliothis virescens (vii) IMMEDIATE SOURCE:
            (B) CLONE: HSCP4343+

(xi) SEQUENCE DESCRIPTION: SEQ ID NO:25:
```

TGGGAGAACT CACCGATGAA CTT                      23

(2) INFORMATION FOR SEQ ID NO:26:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Heliothis virescens (vii) IMMEDIATE SOURCE:
        (B) CLONE: HSC 4325+

(xi) SEQUENCE DESCRIPTION: SEQ ID NO:26:

ATCTTAGAGA ACTACACCTG GGA                      23

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Heliothis virescens (vii) IMMEDIATE SOURCE:
        (B) CLONE: HSC4394-

(xi) SEQUENCE DESCRIPTION: SEQ ID NO:27:

CATGATCTGT ATCCATCCCT                          20

(2) INFORMATION FOR SEQ ID NO:28:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Heliothis virescens (vii) IMMEDIATE SOURCE:
        (B) CLONE: HSC4415+

(xi) SEQUENCE DESCRIPTION: SEQ ID NO:28:

AGGGATGGAT ACAGATCATG AA                       22

(2) INFORMATION FOR SEQ ID NO:29:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Heliothis virescens (vii) IMMEDIATE SOURCE:
             (B) CLONE: HSC4399-

(xi) SEQUENCE DESCRIPTION: SEQ ID NO:29:

GCGTCGTTCA TGATCTGTAT CCA                                           23

(2) INFORMATION FOR SEQ ID NO:30:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: DNA (genomic)

(vi) ORIGINAL SOURCE:
             (A) ORGANISM: Heliothis virescens (vii) IMMEDIATE SOURCE:
             (B) CLONE: HSC4834+

(xi) SEQUENCE DESCRIPTION: SEQ ID NO:30:

CTGAATATCA CGATGAATAT CAT                                           23

(2) INFORMATION FOR SEQ ID NO:31:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: DNA (genomic)

(vi) ORIGINAL SOURCE:
             (A) ORGANISM: Heliothis virescens (vii) IMMEDIATE SOURCE:
             (B) CLONE: SCpu4991+

(xi) SEQUENCE DESCRIPTION: SEQ ID NO:31:

ATHGARAART AYTTYGT                                                  17

(2) INFORMATION FOR SEQ ID NO:32:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: DNA (genomic)

(vi) ORIGINAL SOURCE:
             (A) ORGANISM: Heliothis virescens (vii) IMMEDIATE SOURCE:
             (B) CLONE: HSC5097+

(xi) SEQUENCE DESCRIPTION: SEQ ID NO:32:

TTGTTCGMGC TGGCCAT                                                  17

(2) INFORMATION FOR SEQ ID NO:33:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (genomic)

(vi) ORIGINAL SOURCE:
             (A) ORGANISM: Heliothis virescens (vii) IMMEDIATE SOURCE:
             (B) CLONE: HSC5083-

(xi) SEQUENCE DESCRIPTION: SEQ ID NO:33:

AGTGACATGG CCAGCGCGAA                                                   20

(2) INFORMATION FOR SEQ ID NO:34:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (genomic)

(vi) ORIGINAL SOURCE:
             (A) ORGANISM: Heliothis virescens (vii) IMMEDIATE SOURCE:
             (B) CLONE: HSC5095-

(xi) SEQUENCE DESCRIPTION: SEQ ID NO:34:

AATAAGGCTG GCAGTGACAT                                                   20

(2) INFORMATION FOR SEQ ID NO:35:

(i) SEQUENCE CHARACTERISTICS:
             (A) LENGTH: 15 base pairs
             (B) TYPE: nucleic acid
             (C) STRANDEDNESS: single
             (D) TOPOLOGY: linear (ii) MOLECULE TYPE: DNA (genomic)

(vi) ORIGINAL SOURCE:
             (A) ORGANISM: Heliothis virescens (vii) IMMEDIATE SOURCE:
             (B) CLONE: SCpu5169+

(xi) SEQUENCE DESCRIPTION: SEQ ID NO:35:

GCNATHTTYG GNATG                                                        15

(2) INFORMATION FOR SEQ ID NO:36:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: DNA (genomic)

(vi) ORIGINAL SOURCE:
             (A) ORGANISM: Heliothis virescens (vii) IMMEDIATE SOURCE:
             (B) CLONE: SCpu5143-

(xi) SEQUENCE DESCRIPTION: SEQ ID NO:36:

ATNGCRAADA TRAACAT                                                      17

(2) INFORMATION FOR SEQ ID NO:37:

```
    (i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Heliothis virescens (vii) IMMEDIATE SOURCE:
        (B) CLONE: SCpu5285+

(xi) SEQUENCE DESCRIPTION: SEQ ID NO:37:

TCNGCNGGNT GGGAYGG                                                  17

(2) INFORMATION FOR SEQ ID NO:38:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Heliothis virescens (vii) IMMEDIATE SOURCE:
        (B) CLONE: SCpu5425-

(xi) SEQUENCE DESCRIPTION: SEQ ID NO:38:

AAACGACGGC CAGTGAGACN GCDATRTACA TRTT                               34

(2) INFORMATION FOR SEQ ID NO:39:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Drosophila melanogaster (vii) IMMEDIATE SOURCE:
        (B) CLONE: para 4991+

(xi) SEQUENCE DESCRIPTION: SEQ ID NO:39:

GAAATCACTC CCAATTAATH GARAARTAYT TYGT                               34

(2) INFORMATION FOR SEQ ID NO:40:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Drosophila melanogaster
```

-continued

```
    (vii) IMMEDIATE SOURCE:
          (B) CLONE: para5143-

(xi) SEQUENCE DESCRIPTION: SEQ ID NO:40:

TTTCCCAGTC ACGACATNGC RAADATRAAC AT                                32
```